US011006931B2

(12) United States Patent
Tsushima

(10) Patent No.: US 11,006,931 B2
(45) Date of Patent: May 18, 2021

(54) ULTRASOUND SIGNAL PROCESSING DEVICE AND ULTRASOUND DIAGNOSTIC DEVICE

(71) Applicant: Konica Minolta, Inc., Tokyo (JP)

(72) Inventor: Mineo Tsushima, Kyoto-fu (JP)

(73) Assignee: KONICA MINOLTA, INC., Tokyo (JP)

(*) Notice: Subject to any disclaimer, the term of this patent is extended or adjusted under 35 U.S.C. 154(b) by 801 days.

(21) Appl. No.: 14/989,275

(22) Filed: Jan. 6, 2016

(65) Prior Publication Data

US 2016/0199038 A1 Jul. 14, 2016

(30) Foreign Application Priority Data

Jan. 9, 2015 (JP) .............................. JP2015-002804

(51) Int. Cl.
*A61B 8/08* (2006.01)
*A61B 8/00* (2006.01)
(Continued)

(52) U.S. Cl.
CPC .............. *A61B 8/5276* (2013.01); *A61B 8/14* (2013.01); *A61B 8/4494* (2013.01);
(Continued)

(58) Field of Classification Search
CPC ....... A61B 8/14; A61B 8/4494; A61B 8/5207; A61B 8/5269; A61B 8/5276;
(Continued)

(56) References Cited

U.S. PATENT DOCUMENTS 5,873,830 A * 2/1999 Hossack ............. G01S 7/52046
600/447
6,077,226 A * 6/2000 Washburn ................ A61B 8/06
600/443
(Continued)

FOREIGN PATENT DOCUMENTS

JP 2009-536854 A 10/2009
JP 2014-183922 A * 10/2014

OTHER PUBLICATIONS

Beam Steering [Online]. Olympus Corporation, Apr. 17, 2013 [retrieved on Sep. 19, 2018]. Retrieved from the Internet: <URL:https://web.archive.org/web/20130417153125/http://www.olympus-ims.com:80/en/ndt-tutorials/transducers/pa-beam/steering>. Beam Steering (Linear 0 °) figure.*

(Continued)

*Primary Examiner* — Carolyn A Pehlke
*Assistant Examiner* — Victoria Fang
(74) *Attorney, Agent, or Firm* — Lucas & Mercanti, LLP

(57) ABSTRACT

An ultrasound signal processing device: performing transmission events each involving selecting a group among transducer elements arranged in line in an ultrasound probe, and causing the group to transmit ultrasound towards a subject; for each transmission event, receiving ultrasound reflection from the subject; and generating a frame acoustic line signal based on sub-frame acoustic line signals that are generated based on the ultrasound reflection. The ultrasound signal processing device includes: a calculator that calculates, based on reflected ultrasound, a motion amount indicating movement between image signals for the subject; and a synthesizer generating the frame acoustic line signal based on the sub-frame acoustic line signals. The number of sub-frame acoustic line signals that the synthesizer uses to generate a frame acoustic line signal decreases when the (Continued)

motion amount is equal to or greater than a predetermined threshold.

23 Claims, 24 Drawing Sheets

(51) Int. Cl.
*G10K 11/34* (2006.01)
*A61B 8/14* (2006.01)
*G01S 15/89* (2006.01)
*G01S 7/52* (2006.01)

(52) U.S. Cl.
CPC ........ *A61B 8/5207* (2013.01); *G01S 7/52046* (2013.01); *G01S 15/8915* (2013.01); *G01S 15/8997* (2013.01); *G10K 11/346* (2013.01); *G01S 7/5209* (2013.01)

(58) Field of Classification Search
CPC ............. G01S 7/52046; G01S 15/8915; G01S 15/8997; G01S 7/5209; G10K 11/346
USPC .................................................. 600/443, 437
See application file for complete search history.

(56) References Cited

U.S. PATENT DOCUMENTS

| | | | |
|---|---|---|---|
| 6,132,375 A * | 10/2000 | Napolitano | G01S 7/52046 600/443 |
| 2005/0075569 A1 * | 4/2005 | Li | G01S 15/8995 600/454 |
| 2007/0078326 A1 * | 4/2007 | Yoshikawa | A61B 8/08 600/407 |
| 2009/0069693 A1 * | 3/2009 | Burcher | G01S 7/52028 600/459 |
| 2009/0076369 A1 * | 3/2009 | Mistretta | A61B 6/482 600/407 |
| 2009/0099456 A1 * | 4/2009 | Burcher | A61B 8/00 600/459 |
| 2009/0306512 A1 * | 12/2009 | Loftman | G01S 7/52046 600/447 |
| 2009/0326377 A1 * | 12/2009 | Hirama | G01S 7/52046 600/447 |
| 2010/0150412 A1 * | 6/2010 | Robinson | A61B 8/5276 382/128 |
| 2014/0094700 A1 * | 4/2014 | Watanabe | G10K 11/346 600/437 |
| 2016/0174938 A1 * | 6/2016 | Takano | A61B 8/14 600/459 |
| 2016/0278742 A1 * | 9/2016 | Tsushima | G01S 15/8997 |
| 2016/0338673 A1 * | 11/2016 | Imai | A61B 8/06 |
| 2017/0042510 A1 * | 2/2017 | Ikeda | A61B 8/14 |
| 2018/0011178 A1 * | 1/2018 | Tsushima | G01S 7/52087 |
| 2018/0055486 A1 * | 3/2018 | Tsushima | A61B 8/14 |
| 2018/0161003 A1 * | 6/2018 | Watanabe | A61B 8/00 |

OTHER PUBLICATIONS

Ito, Masayasu et al. Ultrasonic Diagnostic Equipment (Chou On Pa Shin Dan Sō Chi). Translated by LinguaLinx Language Solutions, Inc. Tokyo, Japan: Corona Publishing Co., Ltd., Aug. 26, 2002. pp. 42-45, ISBN: 4-139-07078-5.*
S. I. Nikolov, et al; Virtual ultrasound sources in high resolution imaging; Proc, SPIE—Progress in biomedical optics and imaging; vol. 3; 2002; pp. 395-405.
Notice of Reasons for Refusal dated Mar. 27, 2018 from correponding Japenese Patent Application No. JP 2015-002804 and English translation.

* cited by examiner

ULTRASOUND SIGNAL PROCESSING DEVICE AND ULTRASOUND DIAGNOSTIC DEVICE

CROSS REFERENCE TO RELATED APPLICATION

This Application claims the priority of Japanese Patent Application No. 2015-002804 filed on Jan. 9, 2015, application which is incorporated by reference herein.

BACKGROUND OF THE INVENTION (1) Field of the Invention

The present disclosure is related to an ultrasound signal processing device, and an ultrasound diagnostic device utilizing the ultrasound signal processing device. In particular, the present disclosure relates to beam forming in an ultrasound signal processing device.

(2) Description of the Related Art

Typically, an ultrasound diagnostic device transmits ultrasound towards the inside of a subject via an ultrasound probe (referred to in the following as a "probe"), and receives reflected ultrasound (an echo) via the probe. The reflected ultrasound is generated within the subject due to tissues in the subject having different acoustic impedances. Further, an ultrasound diagnostic device generates an ultrasound tomographic image based on electric signals acquired through the reception of the reflected ultrasound, and displays the ultrasound tomographic image on a monitor (referred to in the following as a "display unit"). An ultrasound tomographic image shows the structures of tissues inside the subject. Ultrasound diagnostic devices are widely used for the shape diagnosis of subjects, for having low invasiveness and achieving real-time observation of tissues through tomographic images and the like.

A typical method applied in conventional ultrasound diagnostic devices for reception beam forming (i.e., forming signals based on received reflected ultrasound (echo signals)) is so-called delay-and-sum (DAS) beam forming. One example of delay-and-sum beam forming can be found disclosed in pages 42-45 of "Ultrasound Diagnostic Device", written by Masayasu Itou and Tsuyoshi Mochizuki and published by Corona Publishing Co., Ltd (Aug. 26, 2002).

FIG. 24 is a schematic illustrating reception beam forming in a conventional ultrasound diagnostic device. The conventional ultrasound diagnostic device illustrated in FIG. 24 includes a probe 201 and a reception beam former 202. The probe 201 includes a plurality of ultrasound transducer elements (referred to in the following as "transducer elements") 201a that receive ultrasound reflection (echo signals) from the subject. The reception beam former 202 electrically converts the reflected ultrasound received by the transducer elements 201a into analog electronic signals, converts the analog electronic signals into digital electronic signals through some amplification and A/D conversion, and performs delaying and summing of the digital electronic signals. The reception beam former 202 includes a plurality of delaying units 2021, and an adding unit 2022. The delaying units 2021 are each associated with a corresponding one of the transducer elements 201a, and performs amplification, A/D conversion, and delaying with respect to an electric signal. The adding unit 2022 provides signals output from the delay units 2021 with weights referred to as so-called apodization weights, and sums the weighted signals. The reception beam former 202 generates and outputs an acoustic line signal by each of the delaying units 2021 performing delaying with respect to an electric signal based on reflected ultrasound obtained by the corresponding transducer element 201a, and by the adding unit 2022 summing the delayed electric signals obtained from the delaying units 2021. Typically, the delay amount that each delaying unit 2021 applies is based on the distance between the corresponding transducer element 201a and the measurement point, which is located along the central axis of the transmitted ultrasound beam.

In specific, suppose that: P denotes a measurement point that is at a given depth inside the subject and that is located along the central axis of the transmitted ultrasound beam; C denotes a transducer element, among the plurality of transducer elements, that is closest to the measurement point P; $d_c$ denotes the distance between the measurement point P and the transducer element C; m denotes a transducer element other than the transducer element C; $d_m$ denotes the distance between the measurement point P and the transducer element m; and cs denotes ultrasound velocity. Here, the time point at which reflected ultrasound from the measurement point P arrives at the transducer element m is later than the time point at which reflected ultrasound from the measurement point P arrives at the transducer element C by ($d_m$/cs–$d_c$/cs). Thus, by calculating the time point at which reflected ultrasound from the measurement point P arrives at the transducer element C, the time point at which reflected ultrasound from the measurement point P arrives at the transducer element m can be calculated based on this difference ($d_m$/cs–$d_c$/cs). As such, each delaying unit 2021 specifies a reception signal for the corresponding transducer element 201a by considering the difference between arrival times of reflected ultrasound, and the adding unit 2022 generates an acoustic line signal by summing the reception signals specified by the delaying units 2021. This reception beam forming method is capable of acquiring high quality ultrasound images with high resolution and low noise around a transmission focal point. A transmission focal point is a point at a given depth in the subject where the wavefront of transmitted ultrasound converges.

SUMMARY OF THE INVENTION

Problems to be Solved by the Invention

Meanwhile, the conventional reception beam forming method has difficulty in acquiring high quality ultrasound images from areas within an ultrasound irradiation area that are far from the transmission focal point. In addition, application of the conventional reception beam forming method may result in motion artifacts, such as image blurs and false images, occurring in ultrasound images in response to movements such as the movement of the body of the subject and the movement of the probe.

In view of such technical problems, the present disclosure provides an ultrasound signal processing device and an ultrasound diagnostic device utilizing the ultrasound signal processing device that are capable of generating high quality ultrasound images (i.e., ultrasound images with high resolution and low noise) with reduced motion artifacts from the entire ultrasound irradiation area.

Means for Solving the Problems

One aspect of the present disclosure is an ultrasound signal processing device (i) performing a sequence of transmission events each involving selecting a first group of transducer elements from among a plurality of transducer elements of an ultrasound probe that are arranged in at least one line along a transducer element array direction, and causing each transducer element in the first group to transmit ultrasound towards a subject; (ii) for each of the transmission events, generating a sub-frame acoustic line signal based on ultrasound reflection received from the subject in response to the transmission event, to yield a plurality of sub-frame acoustic line signals each corresponding to a different one of the transmission events; and (iii) generating a frame acoustic line signal for the sequence based on the sub-frame acoustic line signals for the transmission events, the ultrasound signal processing device including ultrasound signal processing circuitry that operates as: a transmitter that, in each of the transmission events, selects the first group and causes each transducer element in the first group to transmit ultrasound towards the subject, the transmitter selecting the first group such that the first group shifts in the transducer element array direction from one transmission event to another; a receiver that, for each of the transmission events, selects a second group of transducer elements from among the plurality of transducer elements of the ultrasound probe, and generates a reception signal sequence for each transducer element in the second group based on ultrasound reflection received by the transducer element; a target area setter that, for each of the transmission events, sets a target area being a virtual signal area for generating the sub-frame acoustic line signal for the transmission event; a delay-and-sum calculator that, for each of the transmission events, generates the sub-frame acoustic line signal by performing, for each measurement point that is included in the target area for the transmission event, delay-and-sum processing with respect to one or more reception signal sequences generated based on ultrasound reflection received from the measurement point; and a synthesizer generating the frame acoustic line signal for the sequence based on the sub-frame acoustic line signals for the transmission events, and in the ultrasound signal processing device, the ultrasound signal processing circuitry further operates as a motion amount calculator that calculates, based on reflected ultrasound, a motion amount indicating movement between image signals for the subject, and the number of sub-frame acoustic line signals that the synthesizer uses to generate a frame acoustic line signal decreases when the motion amount is equal to or greater than a predetermined threshold.

BRIEF DESCRIPTION OF THE DRAWINGS

These and the other objects, advantages and features of the technology pertaining to the present disclosure will become apparent from the following description thereof taken in conjunction with the accompanying drawings, which illustrate specific embodiments of the technology pertaining to the present disclosure.

In the drawings.

Figure 11:
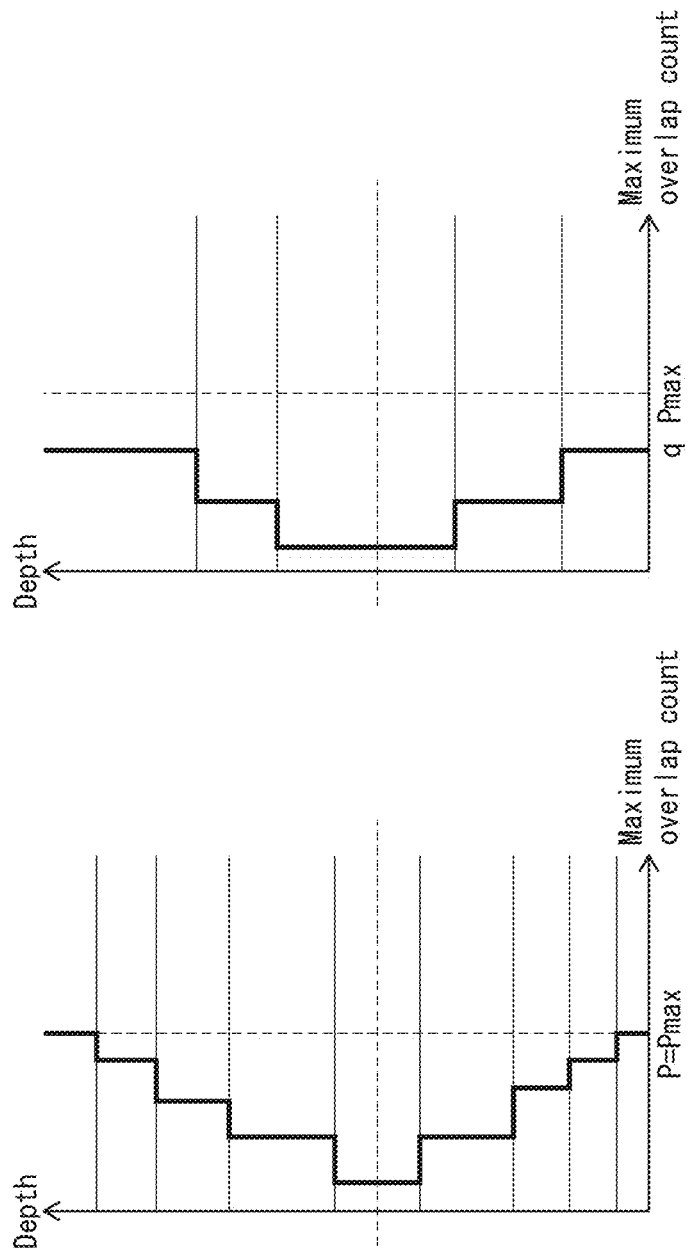
Figure 12:
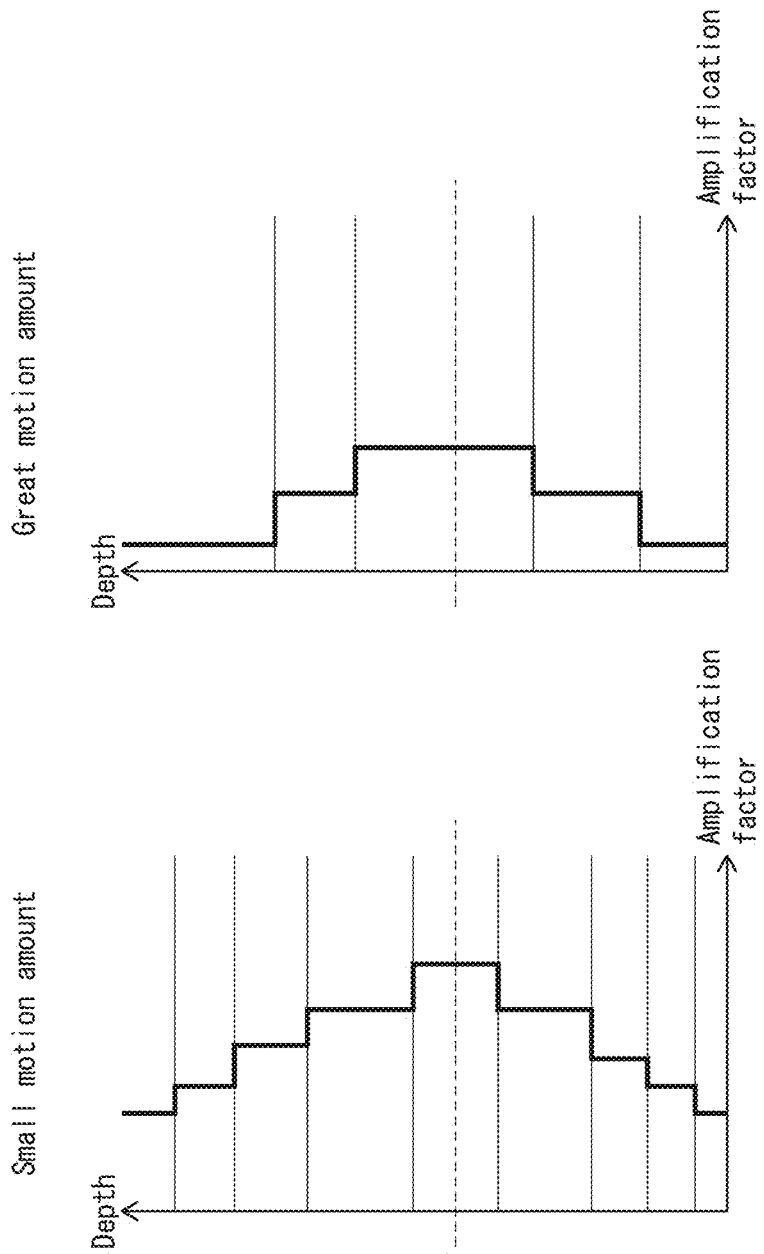
Figure 13:
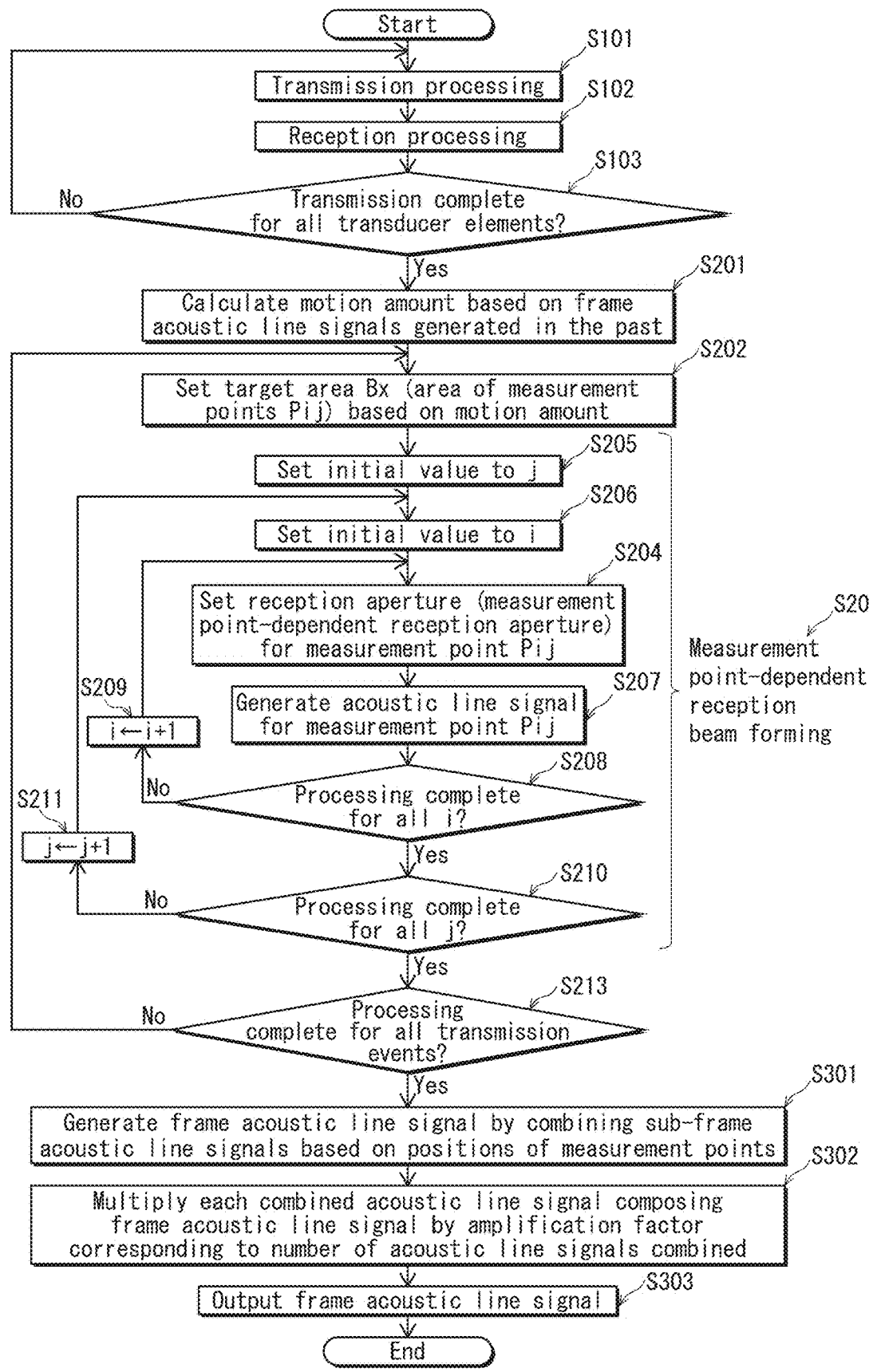
Figure 14:
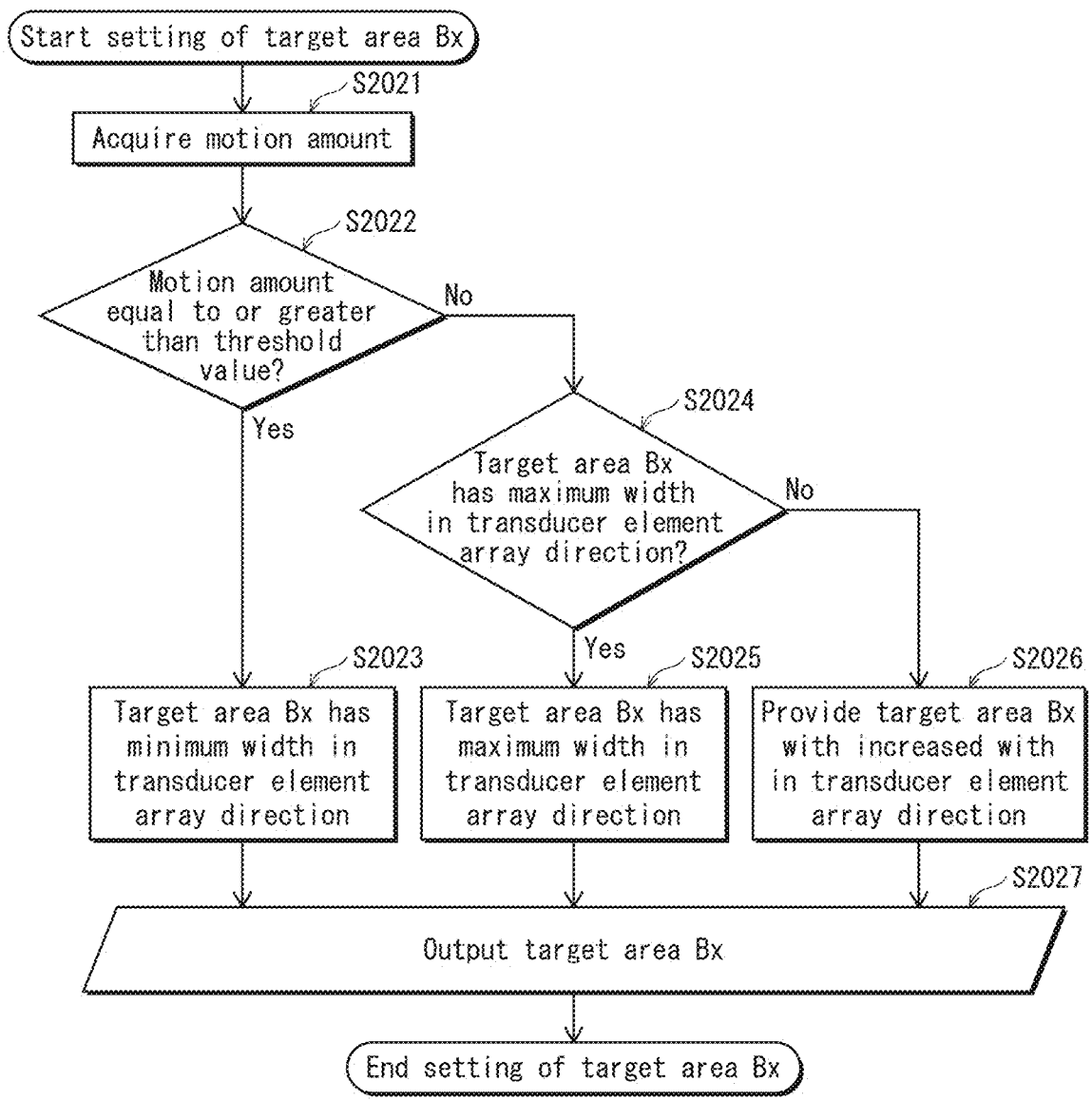
Figure 15:
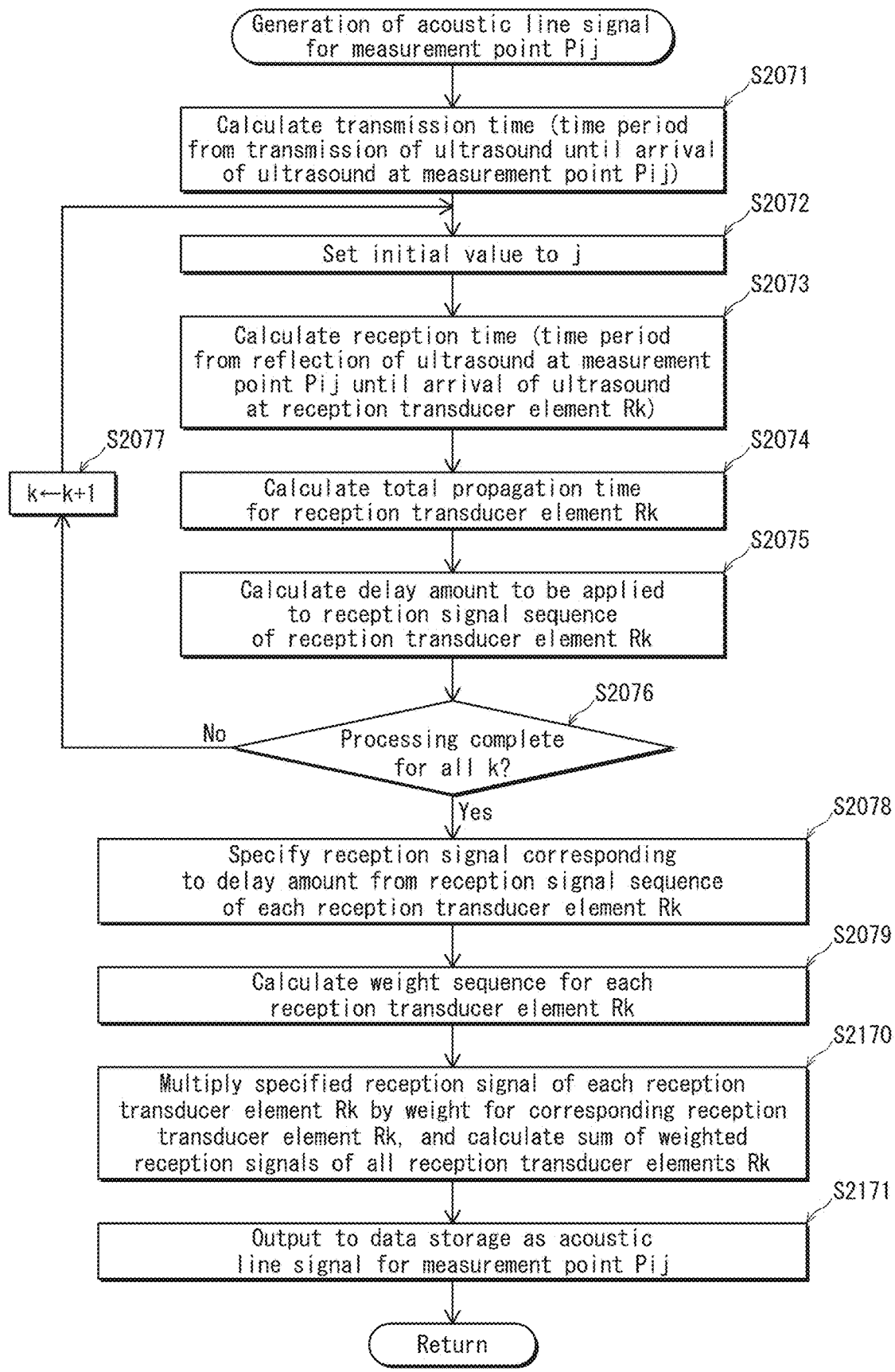
Figure 16:
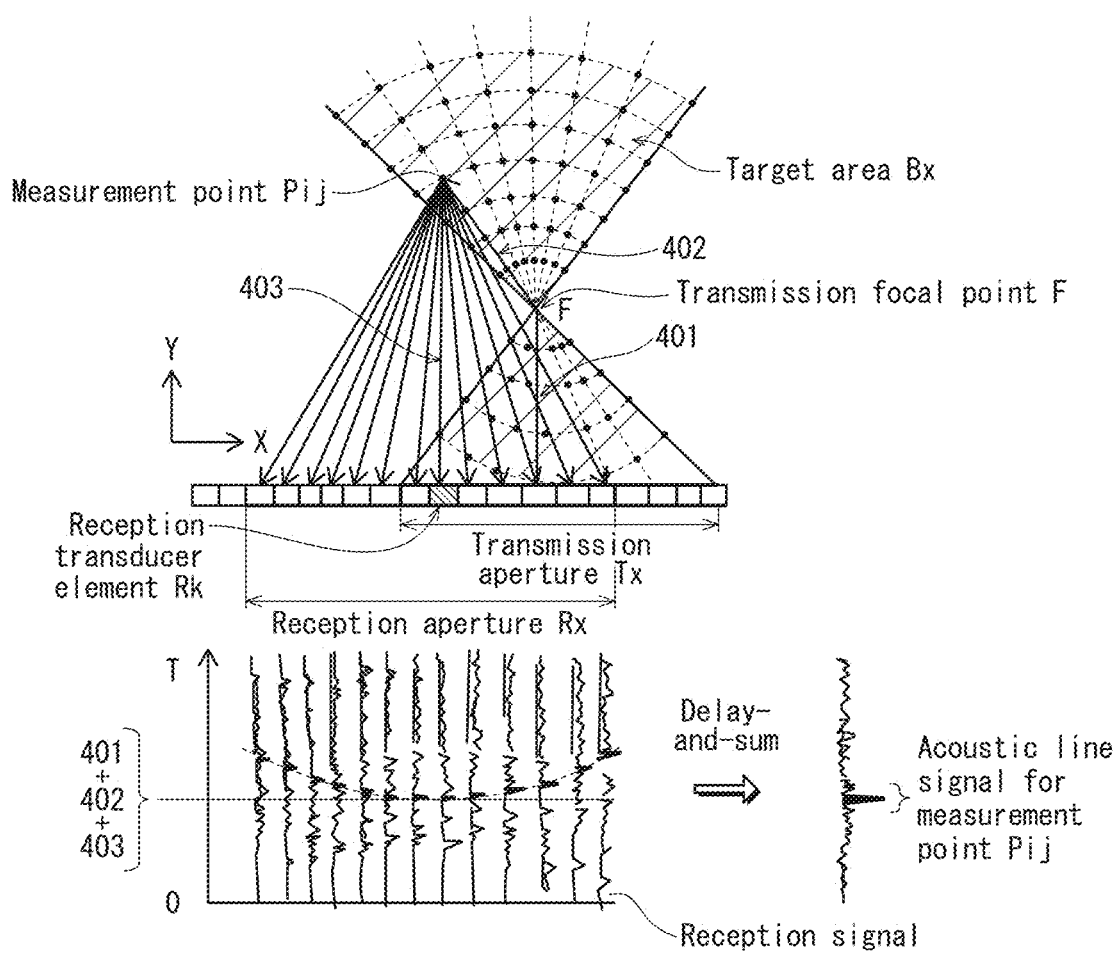
Figure 17:
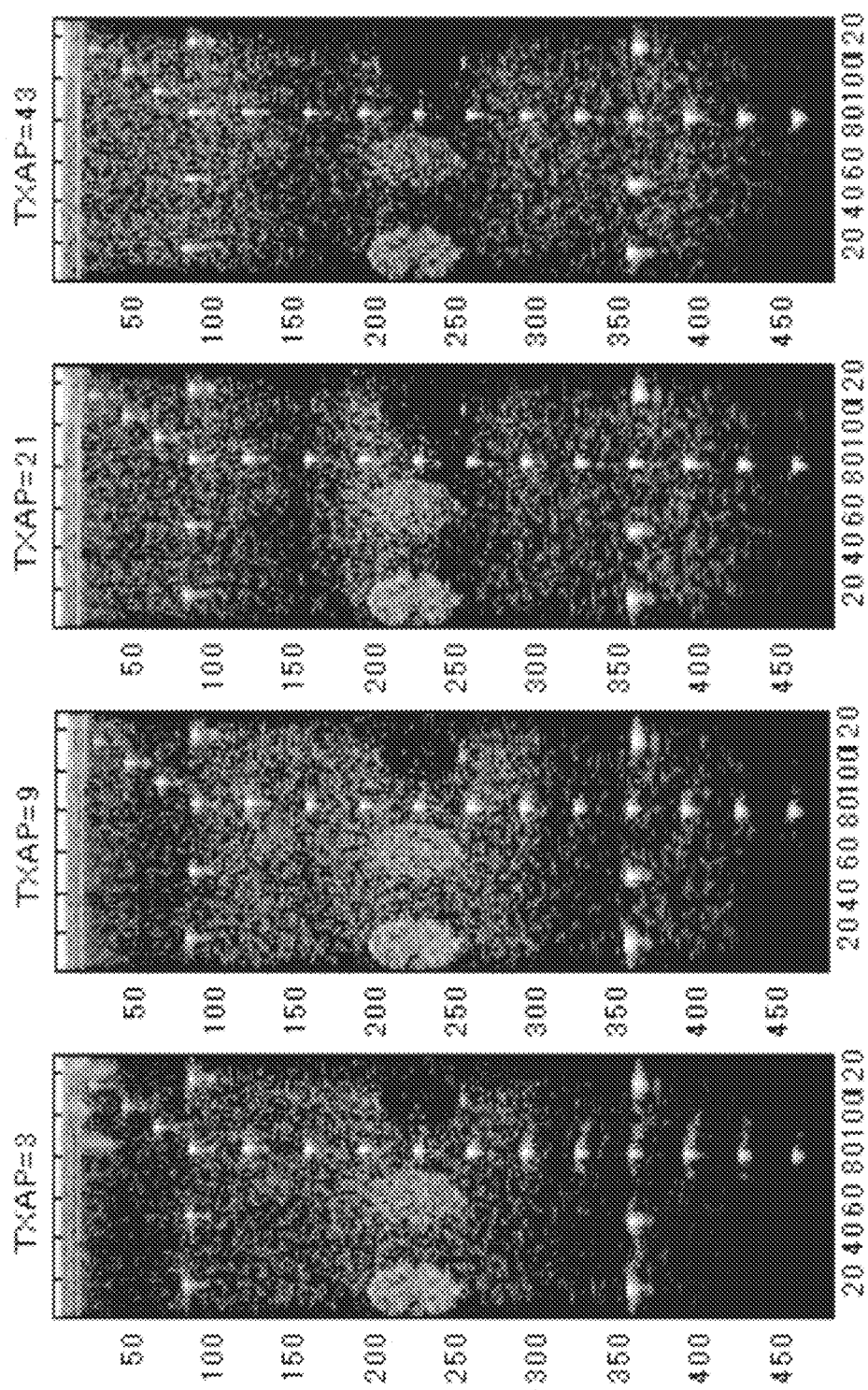
Figure 18:
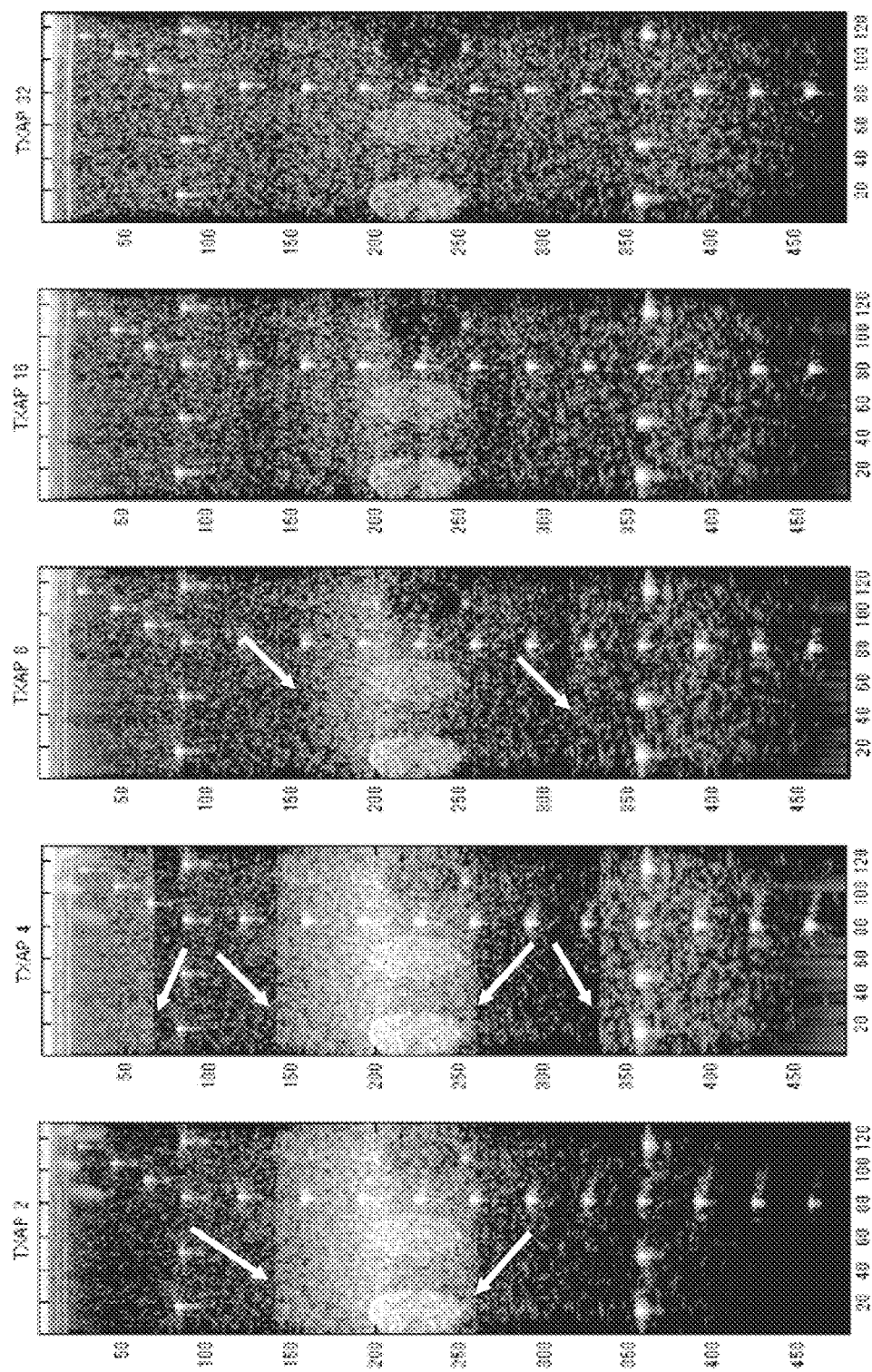
Figure 19:
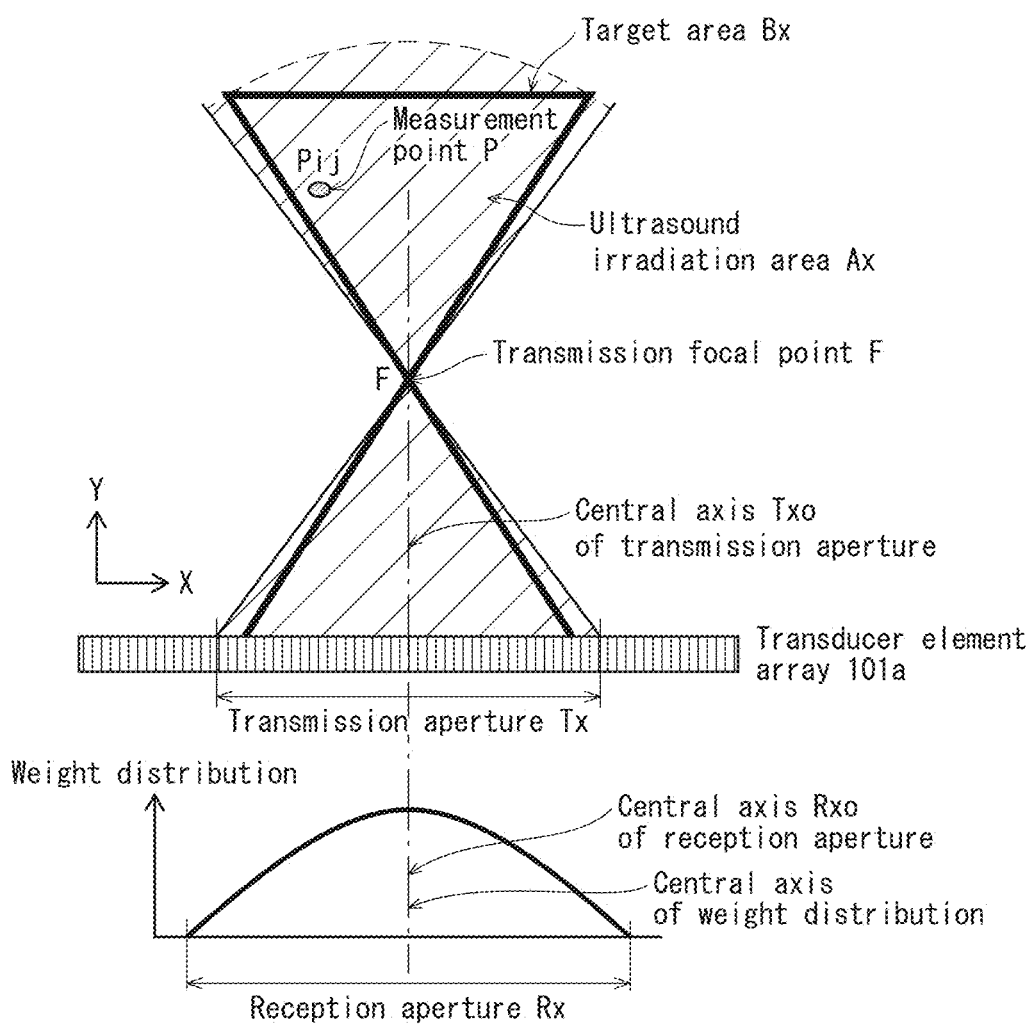
Figure 20:
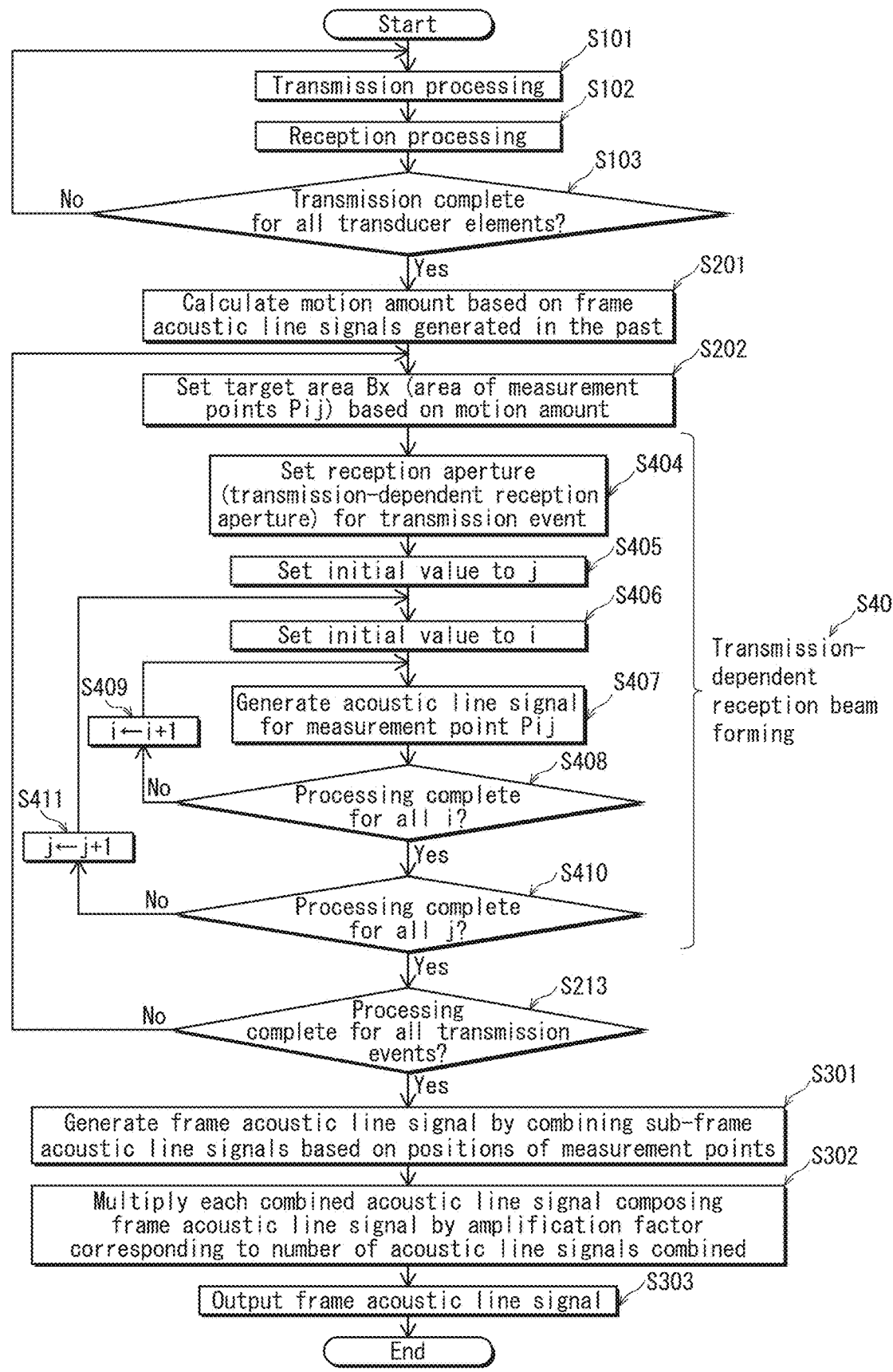
Figure 21:
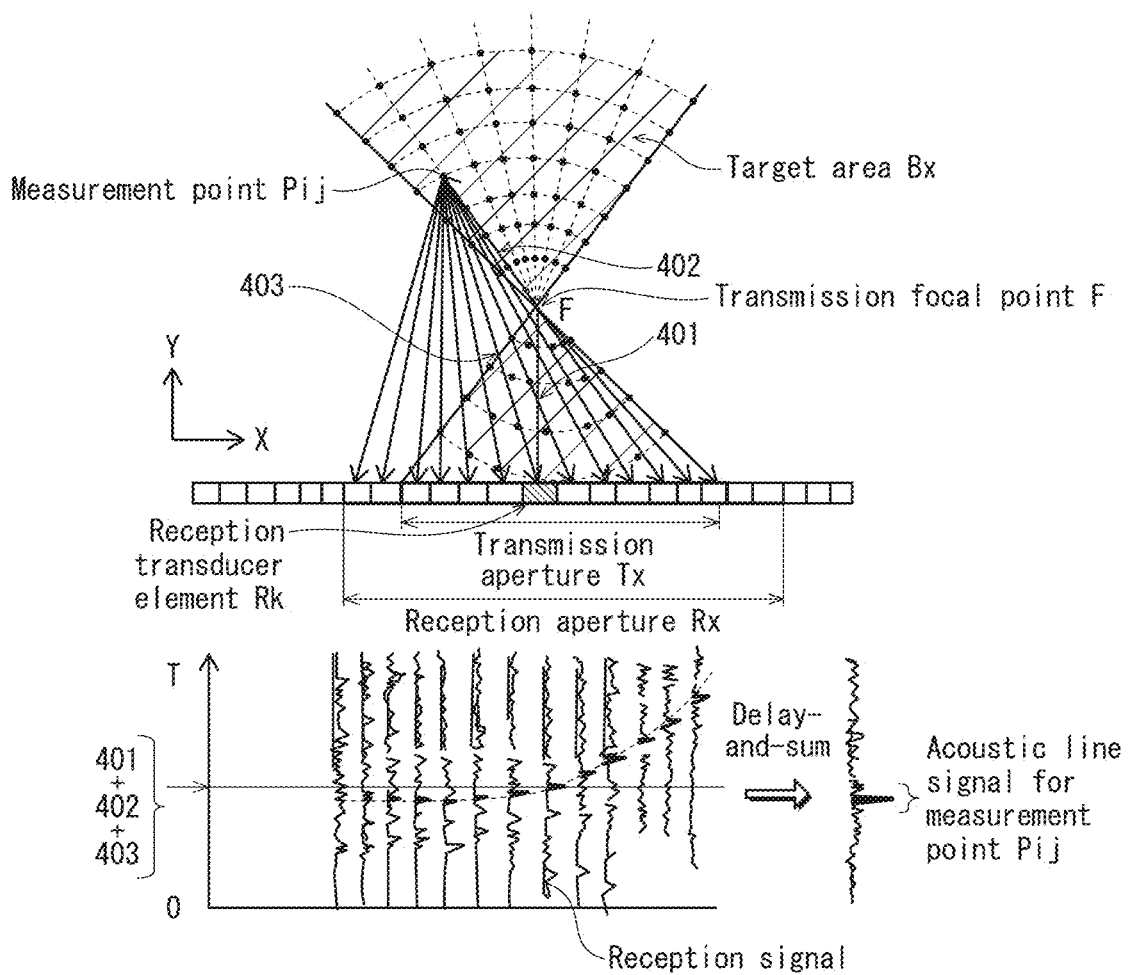
Figure 22:
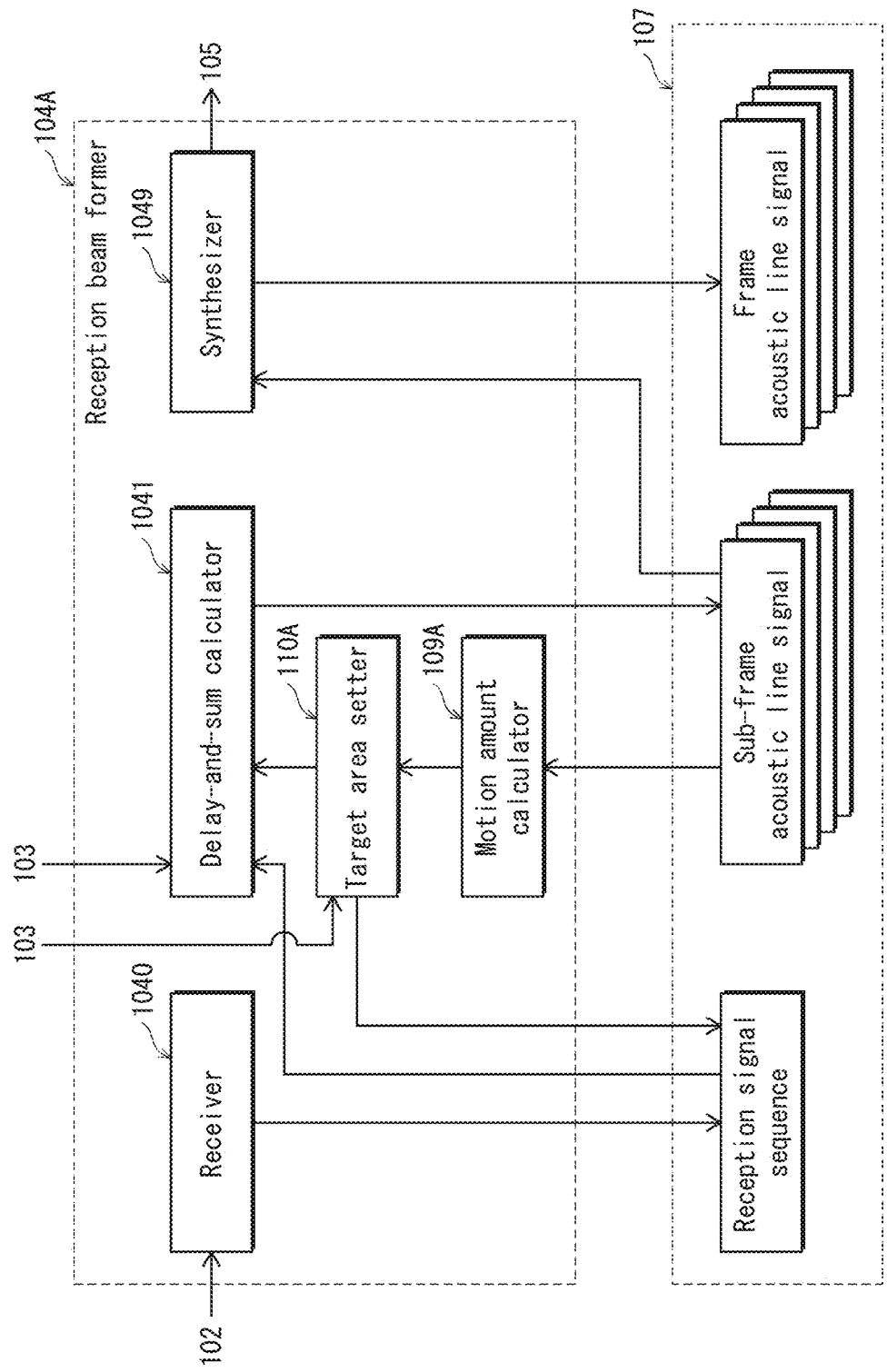
Figure 23:
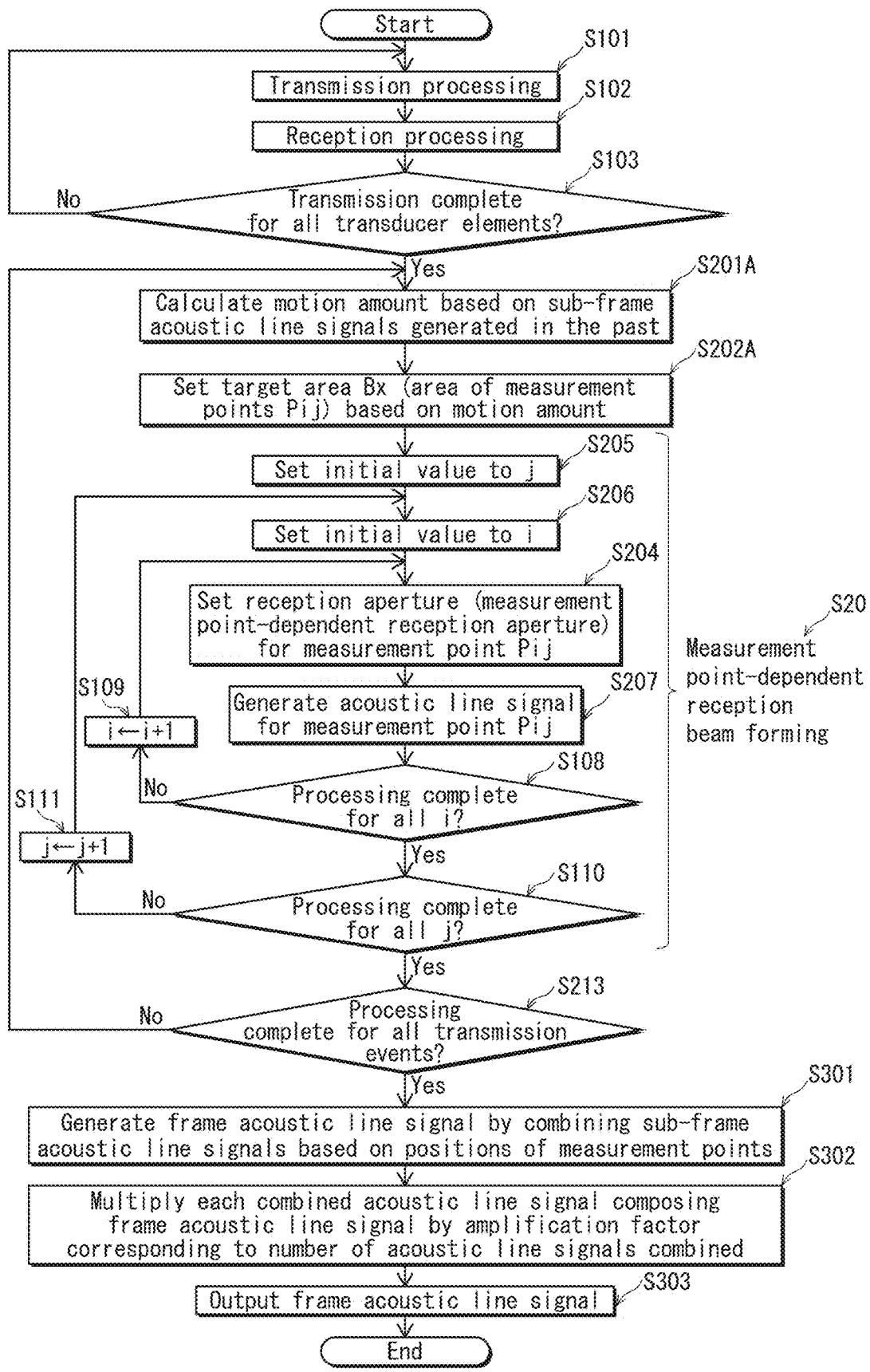
Figure 24:
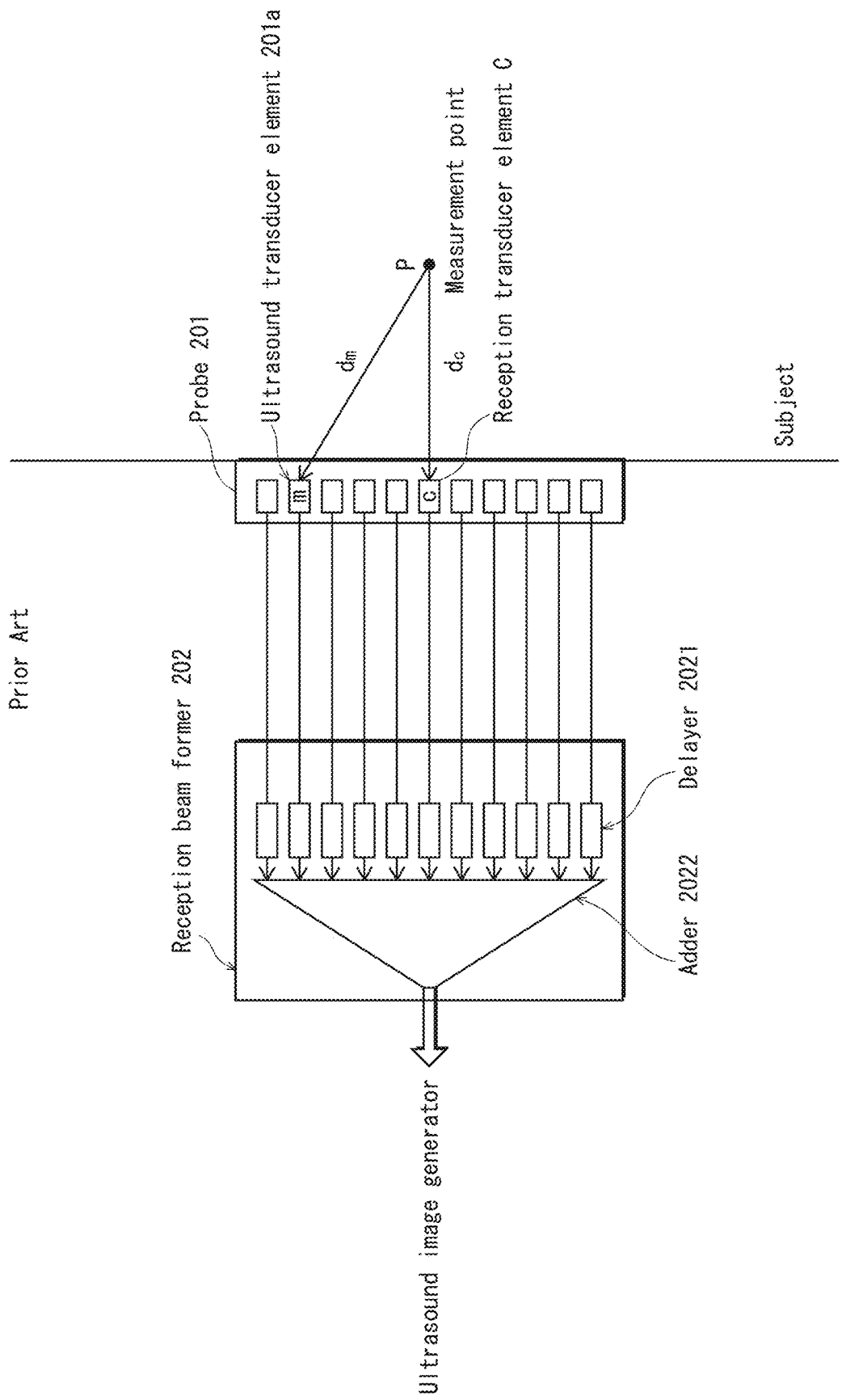

each of FIGS. 11A and 11B is a schematic illustrating a maximum overlap count of the combined acoustic line signal, with FIG. 11A corresponding to a small motion amount and FIG. 11B corresponding to a great motion amount;

each of FIGS. 12A and 12B is a schematic providing an overview of amplification by an amplifier 10492, with FIG. 12A corresponding to a small motion amount and FIG. 12B corresponding to a great motion amount;

FIG. 13 is a flowchart illustrating the operations of the reception beam former 104 for beam forming;

FIG. 14 is a flowchart illustrating how the reception beam former 104 sets the target area Bx;

FIG. 15 is a flowchart illustrating the operations of the reception beam former 104 for generating an acoustic line signal for measurement point Pij;

FIG. 16 is a schematic for explaining the operations of the reception beam former 104 for generating an acoustic line signal for measurement point Pij;

FIG. 17 includes photographs of B-mode images generated by the ultrasound diagnostic device 100 based on frame acoustic line signals;

FIG. 18 includes photographs of B-mode images generated by the ultrasound diagnostic device 100 based on frame acoustic line signals generated without performing the amplification;

FIG. 19 is a schematic illustrating the relationship between a reception aperture Rx set by a reception aperture setter 1042 of an ultrasound diagnostic device pertaining to modification 1 and a transmission aperture Tx;

FIG. 20 is a flowchart illustrating the operations of a reception beam former of the ultrasound diagnostic device pertaining to modification 1 for beam forming;

FIG. 21 is a flowchart illustrating the operations of the reception beam former of the ultrasound diagnostic device pertaining to modification 1 for generating an acoustic line signal for measurement point Pij;

FIG. 22 is a functional block diagram illustrating the structure of a reception beam former 104A of an ultrasound diagnostic device pertaining to embodiment 2;

FIG. 23 is a flowchart illustrating the operations of the reception beam former 104A for beam forming; and FIG. 24 is a schematic for explaining the operations of a reception beam former 202 of a conventional ultrasound signal processing device.

DESCRIPTION OF THE PREFERRED EMBODIMENT

The following describes embodiments of the technology pertaining to the present disclosure.

<How Inventors Arrived at Aspects of Present Disclosure>

The present inventor carried out extensive research for improving resolution and signal-to-noise ratio (SNR) of ultrasound images generated by ultrasound diagnostic devices.

The conventional ultrasound diagnostic device disclosed in "Ultrasound Diagnostic Device" performs transmission beam forming (i.e., transmission of ultrasound by a plurality of transducer elements towards the inside of the subject) such that a transmitted ultrasound beam converges (focuses) at a predetermined depth inside the subject. When performing transmission beam forming in such a manner, the ultrasound beam has high definition when a measurement point P is at or near the transmission focal point, due to the ultrasound beam being relatively focused at or near the transmission focal point. Further, the S/N ratio (here, S denotes echo from measurement point P, and N denotes signals from other areas inside the subject) of ultrasound reflection (echo signals) acquired from such a measurement point is also high, due to high spatial energy density at the measurement point. This results in an acoustic line signal with high resolution and high S/N ratio being acquired, and ultimately, in a high quality ultrasound image being acquired. Meanwhile, even if the measurement point P is located along the central axis of the transmitted ultrasound beam, if the measurement point P is far from the transmission focal point, obtaining a high quality ultrasound image is difficult due to an acoustic line signal acquired from such a measurement point having low resolution and low S/N ratio.

Further, in the conventional ultrasound diagnostic device, the measurement point P is always set along the central axis of the transmitted ultrasound beam. Accordingly, reception beam forming is naturally performed by using only reflected ultrasound from measurement points along the central axis of the transmitted ultrasound beam, without using reflected ultrasound from other areas of the ultrasound irradiation area. Due to this, one ultrasound transmission event generates only one acoustic line signal along the central axis of the transmitted ultrasound beam, and thus, reflected ultrasound is not utilized in an efficient manner.

Meanwhile, a reception beam forming method is being proposed that utilizes a so-called synthetic aperture method to yield high quality images not only from the transmission focal point but also from areas other than the transmission focal point. One example of reception beam forming utilizing the synthetic aperture method can be found disclosed in pages 395 through 405 of "Virtual Ultrasound Sources in High Resolution Ultrasound Imaging", S. I. Nikolov and J. A. Jensen, in Proc, SPIE—Progress in Biomedical Optics and Imaging, Vol. 3, 2002. According to this method, delaying is performed taking into consideration both a propagation path of ultrasound and the amount of time required for reflected ultrasound to arrive at a transducer element by travelling along the propagation path. Thus, the method achieves reception beam forming making use of not only reflected ultrasound from near the transmission focal point but also reflected ultrasound from areas of the ultrasound irradiation area other than near the transmission focal point. Due to this, the method enables generating, from one ultrasound transmission event, acoustic line signals covering the entire ultrasound irradiation area, including areas far from the transmission focal point. In addition, the synthetic aperture method enables setting a virtual transmission focal point based on multiple reception signals acquired for one measurement point P through multiple transmission sessions. Thus, the synthetic aperture method enables acquiring an ultrasound image with higher resolution and higher S/N ratio than the reception beam forming method disclosed in "Ultrasound Diagnostic Device".

When reception beam forming utilizing the synthetic aperture method is performed, typically, motion artifacts such as image blurs and false images are likely to occur in ultrasound images, in response to movements such as the movement of the body of the subject and the movement of the subject and the probe with respect to one another (e.g., the movement of the probe). Meanwhile, in the conventional reception beam forming method disclosed in "Ultrasound Diagnostic Device", a frame ultrasound image is composed of a set of signals each corresponding to one linear acoustic line signal or a small number of linear acoustic line signals. Thus, with the conventional reception beam forming method disclosed in "Ultrasound Diagnostic Device", not much image quality degradation is brought about by motion artifacts deriving from movements, such as the movement of the body of the subject and the movement of the probe. That is, even though motion artifacts do occur with the conventional reception beam forming method disclosed in "Ultrasound Diagnostic Device", the influence brought about by motion artifacts is less significant compared with the reception beam forming utilizing the synthetic aperture method. Thus is since a frame ultrasound image is composed of only a small number of linear acoustic line signals in the conventional reception beam forming method disclosed in "Ultrasound Diagnostic Device".

Meanwhile, when applying the synthetic aperture method, a frame ultrasound image is generated by using, for each of a plurality of measurement points P, a plurality of reception signals for the same measurement point that are acquired from different transmission events. Thus, when movement such as the movement of the body of the subject or the movement of the probe occurs during one transmission event or between different transmission events, reception signals acquired from the same measurement point may actually be acquired from different positions. Thus, conventional reception beam forming utilizing the synthetic aperture method not necessarily yields ultrasound images with sufficient image quality, due to a greater amount of motion artifacts such as image blurs and false images that result from movement in ultrasound images occurring with conventional reception beam forming utilizing the synthetic aperture method than with the conventional reception beam forming disclosed in "Ultrasound Diagnostic Device". Thus, it can be said that motion artifacts resulting from movement in ultrasound images are characteristic to the synthetic aperture method.

In view of such technical problems, the present inventor conducted research and development for a technology allowing ultrasound images with high resolution, with high signal S/N ratio, and with reduced motion artifacts to be generated through reception beam forming according to the synthetic aperture method.

The following describes the ultrasound signal processing device and the ultrasound diagnostic device including the ultrasound signal processing device, each of which pertaining to one aspect of the present disclosure in detail.

Embodiment 1

<Overall Structure>

The following describes an ultrasound diagnostic device 100 pertaining to embodiment 1, with reference to the accompanying drawings.

Figure 1:
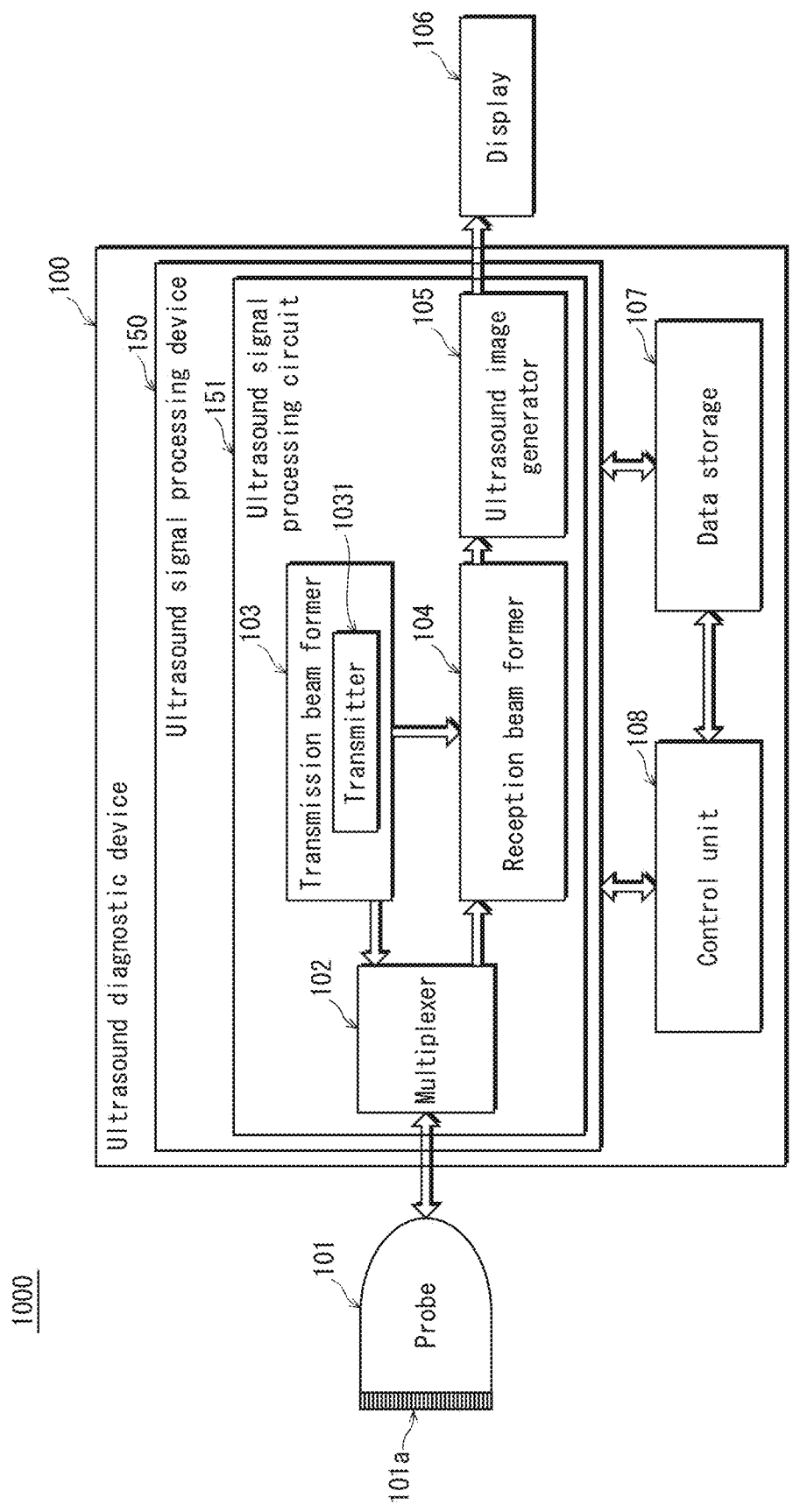
FIG. 1 is a functional block diagram illustrating the structure of an ultrasound diagnostic device 100 pertaining to embodiment 1.

FIG. 1 illustrates functional blocks of the ultrasound diagnostic device pertaining to embodiment 1 (an ultrasound diagnostic system 1000). As illustrated in FIG. 1, the ultrasound diagnostic system 1000 includes: a probe 101; an ultrasound diagnostic device 100; and a display unit 106. The probe 101 includes a plurality of transducer elements 101a. Each of the transducer elements 101a transmits ultrasound towards the subject and receives reflected ultrasound (echo signals). The ultrasound diagnostic device 100 causes the probe 101 to perform transmission/reception of ultrasound, and generates an ultrasound image based on signals output from the probe 101. The display unit 106 displays the ultrasound image on any display device provided thereto. The probe 101 and the display unit 106 are separately connectable to the ultrasound diagnostic device 100. FIG. 1 illustrates the ultrasound diagnostic device 100 with the probe 101 and the display unit 106 connected thereto. Alternatively, the ultrasound diagnostic device 100 may include therein the probe 101 and the display unit 106.

<Structure of Ultrasound Diagnostic Device 100>

The ultrasound diagnostic device 100 includes a multiplexer 102; a transmission beam former 103; and a reception beam former 104. The multiplexer 102 selects one or more of the transducer elements 101a for ultrasound transmission and one or more of the transducer elements 101a for ultrasound reception. The multiplexer 102 may select different ones of the transducer elements 101a for ultrasound transmission and ultrasound reception. Further, the multiplexer 102 provides the transducer elements 101a for ultrasound transmission with input, and receives output from the transducer elements 101a for ultrasound reception. The transmission beam former 103 controls timings of application of a high voltage for ultrasound transmission to each of the transducer elements 101a for ultrasound transmission. The reception beam former 104 performs some amplification and A/D conversion on electric signals yielded by the transducer elements 101a for ultrasound reception, based on reflected ultrasound received by the probe 101, and performs reception beam forming to generate acoustic line signals. In addition, the ultrasound diagnostic device 100 includes an ultrasound image generator 105; a data storage 107; and a control unit 108. The ultrasound image generator 105 generates an ultrasound image (a B-mode image) based on signals output from the reception beam former 104. The data storage 107 stores acoustic line signals output from the reception beam former 104 and ultrasound images output from the ultrasound image generator 105. The control unit 108 controls each of the other constituent elements of the ultrasound diagnostic device 100.

Among the constituent elements of the ultrasound diagnostic device 100, the multiplexer 102, the transmission beam former 103, the reception beam former 104, and the ultrasound image generator 105 constitute an ultrasound signal processing circuit 151, and the ultrasound signal processing circuit 151 constitutes an ultrasound signal processing device 150.

Each constituent element of the ultrasound diagnostic device 100, for example, each of the multiplexer 102, the transmission beam former 103, the reception beam former 104, the ultrasound image generator 105, and the control unit 108 may be implemented by using a hardware circuit such as a field-programmable gate array (FPGA), an application-specific integrated circuit (ASIC), or the like. Alternatively, each of the constituent elements may be implemented by using a combination of software and a programmable device such as a central processing unit (CPU), a General-purpose computing on graphics processing unit (GPGPU), or any processor. Each of such constituent elements may be implemented as one circuit component, or as an aggregate of a plurality of circuit components. Further, a plurality of such constituent elements may be implemented by using one circuit component, or as an aggregate of a plurality of circuit components.

The data storage 107 is a computer-readable recording medium. For example, the data storage 107 may be implemented by using a flexible disk, a hard disk, an MO, a DVD, a DVD-RAM, or a semiconductor memory. Alternatively, the data storage 107 may by an external storage device connected to the ultrasound diagnostic device 100.

Note that the ultrasound diagnostic device 100 pertaining to the present embodiment need not have the structure illustrated in FIG. 1. For example, the ultrasound diagnostic device 100 need not include the multiplexer 102. Further, the probe 101 may have built-in therein a part or the entirety of each of the transmission beam former 103, the reception beam former 104, and the like.

<Structure of Main Part of Ultrasound Diagnostic Device 100>

The ultrasound diagnostic device 100 pertaining to embodiment 1 is characterized for including the transmission beam former 103 and the reception beam former 104. The transmission beam former 103 causes transducer elements 101a of the probe 101 to transmit ultrasound. The reception beam former 104 performs computation with respect to electric signals acquired through the reception of reflected ultrasound by the probe 101, and generates acoustic line signals used in forming an ultrasound image. Accordingly, the present disclosure focuses on the structure and the functions of each of the transmission beam former 103 and the reception beam former 104. Note that components other than the transmission beam former 103 and the reception beam former 104 may have structures and functions similar to those in conventional ultrasound diagnostic devices. In other words, the ultrasound diagnostic device 100 may be implemented by replacing beam formers in a conventional ultrasound diagnostic device with the beam formers pertaining to the present embodiment.

The following describes the structure of each of the transmission beam former 103 and the reception beam former 104.

1. Transmission Beam Former 103

The transmission beam former 103 is connected to the probe 101, via the multiplexer 102. However, note that the multiplexer is not a mandatory element in the present disclosure. The transmission beam former 103 controls timings of application of high voltage with respect to each of a plurality of transducer elements 101a composing a transmission aperture Tx. The transmission aperture Tx is an array of transducer elements composed of all or some of the transducer elements 101a of the probe 101. Note that in the following, the term "transmission transducer element" is used to refer to transducer elements composing the transmission aperture Tx. The transmission beam former 103 includes a transmitter 1031.

The transmitter 1031 performs transmission processing. The transmission processing involves supplying a transmission signal having a pulsar waveform to each of the transmission transducer elements. A transmission transducer element receiving a transmission signal transmits an ultrasound beam. The transmitter 1031 supplies transmission signals to the transmission transducer elements based on transmission control signals output from the control unit 108. In specific, the transmitter 1031 includes, for example, a clock generation circuit, a pulse generation circuit, and a delay circuit.

The clock generation circuit generates a clock signal specifying the transmission timing of ultrasound beams. The pulse generation circuit generates pulse signals for driving the transmission transducer elements. The delay circuit performs focus processing so that ultrasound beams are appropriately focused. In specific, the delay circuit sets a delay time for each transmission transducer element, and delays the transmission of the ultrasound beam from the transmission transducer element by the corresponding delay time.

The transmitter 1031 repetitively performs ultrasound transmission while shifting the transmission aperture Tx in the transducer element array direction each time, so that all of the transducer elements 101*a* of the probe 101 transmit ultrasound. Further, each time ultrasound transmission has been completed, the transmitter 1031 outputs information indicating the positions of transmission transducer elements composing the transmission aperture Tx to the data storage 107, via the control unit 108. For example, supposing that the probe 101 has one hundred and ninety two (192) transducer elements 101*a* in total, the number of transmission transducer elements composing the transmission aperture Tx may be twenty (20) to one hundred (100). In the following, ultrasound transmission by the transmitter 1031, performed by using one transmission aperture (i.e., one set of transmission transducer elements of the predetermined number) is referred to as a transmission event.

Figure 2:
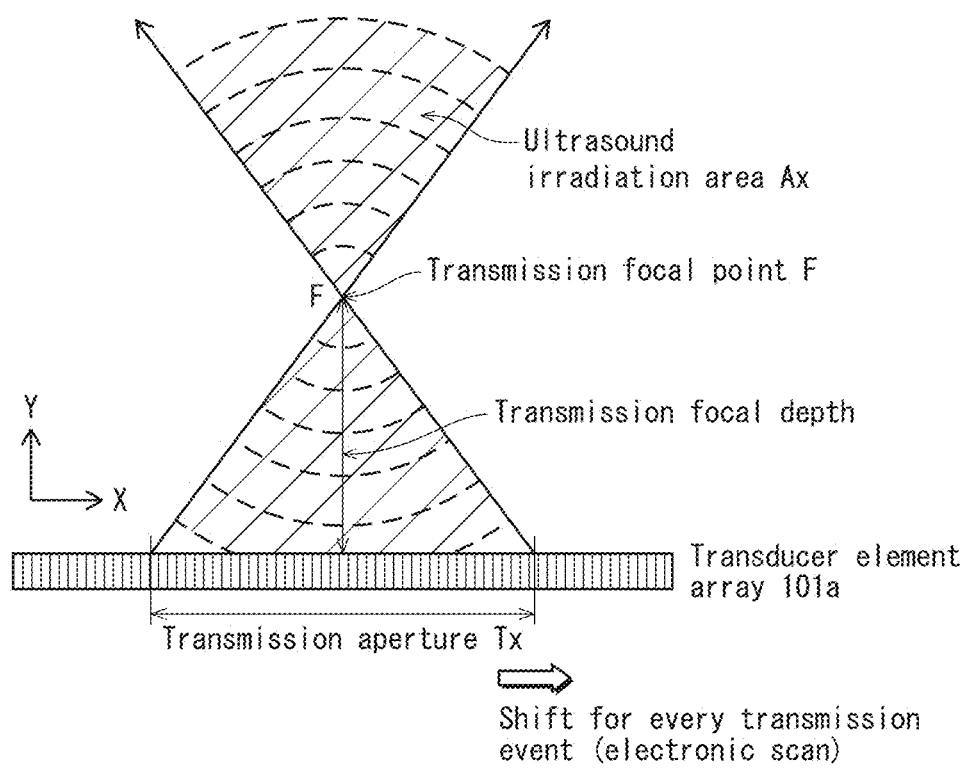
FIG. 2 is a schematic illustrating a propagation path of ultrasound transmitted from a transmission beam former 103.

FIG. 2 is a schematic illustrating a propagation path of an ultrasound beam formed by the transmission beam former 103. FIG. 2 illustrates a transmission aperture Tx for one transmission event (i.e., a transmission transducer element array composed of transmission transducer elements 101*a* that contribute to ultrasound transmission in the transmission event). Further, the transmission-array direction length of the transmission aperture Tx is considered the length of the transmission aperture Tx.

The transmission beam former 103 controls ultrasound transmission by the transmission transducer elements such that a transmission transducer element closer to the center position of the transmission aperture Tx transmits ultrasound later in the transmission event. Due to this, a wavefront of ultrasound transmitted from the transmission transducer elements composing the transmission aperture Tx converges at one point at a certain focal depth in the subject (i.e., the transmission focal point F). Note that the depth of the focal point F (i.e., focal depth) can be set as desired or required. After converging at the focal point F, the wavefront of the transmitted ultrasound expands as before converging at the focal point F. Thus, the transmitted ultrasound waves propagate through an hourglass-shaped area whose base is defined by the transmission aperture Tx and which is partitioned from other areas inside the subject by two straight lines intersecting at the transmission focal point F. That is, ultrasound transmitted from the transmission aperture Tx propagates in the following manner. As the transmitted ultrasound advances in a depth direction of the subject from the transmission aperture Tx, the width thereof (length along horizontal axis (X axis) in FIG. 2) gradually decreases until reaching the minimum width at the transmission focal point F. Then, as the transmitted ultrasound advances further in the depth direction from the transmission focal point F (i.e., as the ultrasound advances in the upward direction in FIG. 2), the width thereof increases (i.e., the ultrasound spreads out). In the following, the hourglass-shaped area described above, which is indicated by hatching in slanted lines in FIG. 2, is referred to as an ultrasound irradiation area Ax.

2. Reception Beam Former 104

Figure 3:
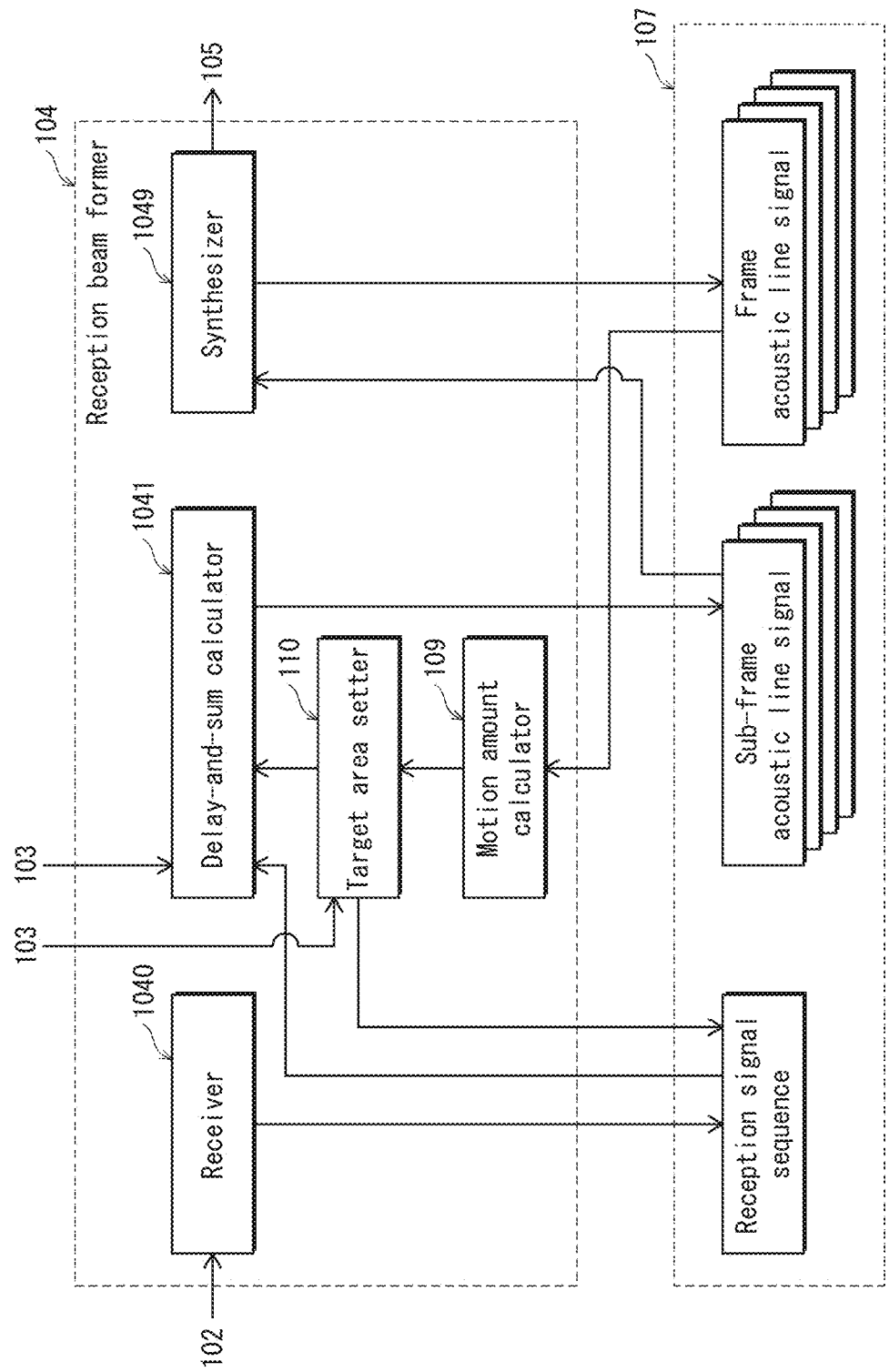
FIG. 3 is a functional block diagram illustrating the structure of a reception beam former 104.

The reception beam former 104 generates acoustic line signals from electric signals acquired by a plurality of transducer elements 101*a*. The transducer elements 101*a* acquire the electric signals based on reflected ultrasound received by the probe 101. Here, an acoustic line signal for one measurement point is generated by performing delay-and-sum processing with respect to reception signals from the measurement point. Description of the delay-and-sum processing is provided later in the present disclosure. FIG. 3 is a functional block diagram illustrating the structure of the reception beam former 104. As illustrated in FIG. 3, the reception beam former 104 includes: a receiver 1040; a delay-and-sum calculator 1041; a target area setter 110; a motion amount calculator 109; and a synthesizer 1049.

The following describes the structure of each functional block of the reception beam former 104.

(1) Receiver 1040

The receiver 1040 is connected to the probe 101, via the multiplexer 102. However, note that the multiplexer is not a mandatory element in the present disclosure. For each transmission event, the receiver 1040 generates reception signals (RF signals). The receiver 1040 generates the reception signals by first amplifying electric signals acquired through the probe 101 receiving reflected ultrasound, and then performing A/D conversion on the amplified signals. The receiver 1040 performs the generation of reception signals for each transmission event, and outputs the reception signals to be stored in the data storage 107.

Here, the receiver 1040 generates one reception signal sequence (RF signal) for each of some or all of the transducer elements 101*a* of the probe 101. In specific, a reception signal sequence for a given transducer element is a digital signal yielded by performing A/D conversion on an electrical signal yielded through conversion of reflected ultrasound received by the transducer element, and is a sequence of signals along the ultrasound transmission direction (corresponding to the depth direction) that are received by the transducer element.

As discussed above, in each transmission event, the transmitter 1031 causes the plurality of transmission transducers composing the transmission aperture Tx, among the transducers 101*a* of the probe 101, each to transmit an ultrasound beam. Meanwhile, for each ultrasound transmission event, the receiver 1040 generates a reception signal sequence for each of some or all of the plurality of transducer elements 101*a* of the probe 101. The generation of the reception signal sequence for a given one of the transducer elements 101*a* is based on reflected ultrasound yielded by the given transducer element 101*a*. Note that in the following, each transducer element receiving reflected ultrasound is referred to as a receive transducer element. Here, it is preferable that the number of receive transducer elements be greater than the number of transmission transducer elements composing the transmission aperture Tx. Further, all of the transducer elements 101*a* of the probe 101 may be used as receive transducer elements.

Further, as already discussed above, the transmitter 1031 repetitively performs transmission events while shifting the transmission aperture Tx in the transducer element array direction each time, so that all of the transducer elements 101*a* of the probe 101 transmit ultrasound. Meanwhile, for each ultrasound transmission event, the receiver 1040 generates a reception signal sequence for each receive transducer element, and stores the reception signal sequences to the data storage 107.

(2) Motion Amount Calculator 109

The motion amount calculator 109 performs image analysis on frame acoustic line signals already stored in the data storage 107 to calculate a motion amount from the frame acoustic line signals. Here, a motion amount calculated from the frame acoustic line signals indicates the movement of image signals for the subject between the frame acoustic line signals. Here, a frame is a unit of signals necessary for forming one ultrasound image. Further, one frame acoustic line signal is a combination of a plurality of acoustic line signals corresponding to one frame. The motion amount calculator 109 calculates a motion amount from frame acoustic line signals by, for example, comparing the frame acoustic line signals and calculating differences between corresponding image areas (composed of one or more pixels) of the frame acoustic line signals, in terms of signal intensity, luminance, and/or the like. Here, it is preferable that the frame acoustic line signals used in motion amount calculation be frame acoustic line signals that have been recently generated, among the frame acoustic line signals stored in the data storage 107. For example, the motion amount calculator 109 may use two frame acoustic line signals most recently generated for motion amount calculation, and compare a frame acoustic line signal generated later among the two with a frame acoustic line signal generated earlier among the two.

In the present embodiment, the motion amount calculator 109 acquires two frame acoustic line signals corresponding to different time points from the data storage 107, and performs motion amount calculation by calculating a difference between the two frame acoustic line signals, in terms of signal intensity, luminance, and/or the like. Alternatively, the motion amount calculator 109 may perform motion amount calculation based on luminance signals. Here, the term luminance signal is used to indicate an ultrasound image signal corresponding to one frame that is acquired through performing gain processing, logarithmic transformation, and/or the like on a frame acoustic line signal.

Figure 4:
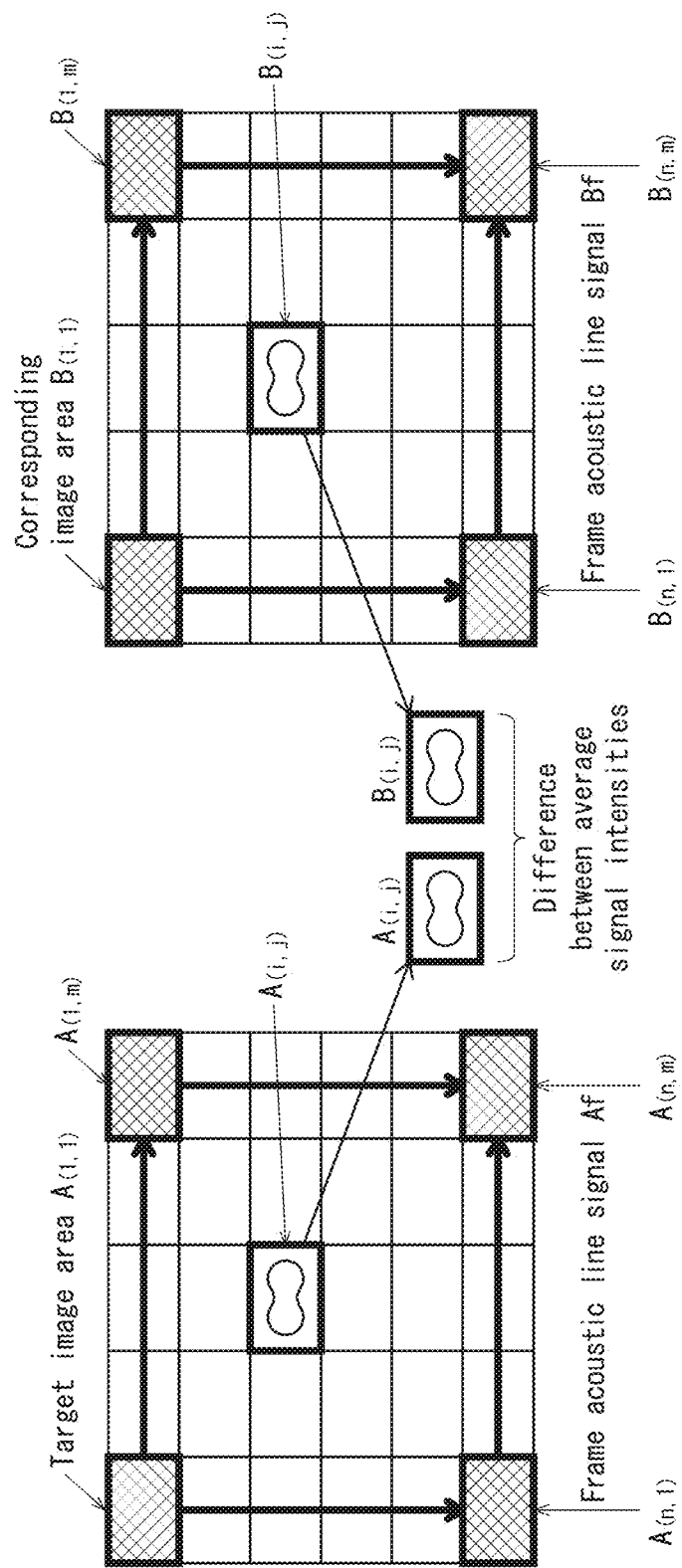
FIG. 4 is a schematic illustrating one example of how a motion amount calculator 109 calculates a motion amount.

FIG. 4 is a schematic illustrating one example of how the motion amount calculator 109 calculates a motion amount. FIG. 4 illustrates an example where the motion amount calculator 109 reads out a frame acoustic line signal Af and a frame acoustic line signal Bf from the data storage 107 and compares the frame acoustic line signal Af (current processing target) with the frame acoustic line signal Bf. Here, note that the frame acoustic line signal Bf is assumed as having been generated earlier in time than the frame acoustic line signal Af. In specific, the motion amount calculator 109 divides the frame acoustic line signal Af into small blocks, having rectangular shapes for example, or in other words, into image areas $A_{(1,1)}$ through $A_{(n,m)}$ (where n and m are integers). Further, the motion amount calculator 109 performs block-by-block comparison by comparing a target image area (expressible as $A_{(i,j)}$, where $1 \leq i \leq n$, $1 \leq j \leq m$) with a corresponding image area in the frame acoustic line signal Bf (expressible as $B_{(i,j)}$, where $1 \leq i \leq n$, $1 \leq j \leq m$), and thereby calculates a difference between the two image areas, in terms of average signal intensity (e.g., luminance, signal power, sum of absolute amplitude values). The motion amount calculator 109 regards that the greater the difference between the two image areas, the greater the movement between corresponding image areas of the two frame acoustic line signals. The motion amount calculator 109 calculates a motion amount in this way for each of the image areas $A_{(1,1)}$ through $A_{(n,m)}$ in the acoustic line signal Af by setting each of the image areas as a target image area, one at a time. Further, the motion amount calculator 109 sums the motion amounts for the image areas $A_{(1,1)}$ through $A_{(n,m)}$ to calculate a total motion amount for the frame acoustic line signal Af.

Alternatively, the motion amount calculator 109 may perform the motion amount calculation by adopting a conventional technology other than the technology discussed above. For example, the motion amount calculator 109 may use processing commonly referred to as "block matching" to detect a direction and an amount of movement between image areas included in the frame acoustic line signals. The motion amount calculator 109, when performing block matching, divides the frame acoustic line signal Af into small blocks having rectangular shapes for example, or in other words, into image areas $A_{(1,1)}$ through $A_{(n,m)}$. Further, the motion amount calculator 109 performs block-by-block comparison by comparing a target image area $A_{(i,j)}$ with image areas $B_{(1,1)}$ through $B_{(an,bm)}$ (where a and b represent coefficients) in the frame acoustic line signal Bf, and thereby calculates a similarity between the target image area in the frame acoustic line signal Af and each image area in the frame acoustic line signal Bf through cross-correlation processing, for example. Here, the motion amount calculator 109 may determine that the smaller the sum of differences between pixels in the target image area in the frame acoustic line signal Af and pixels in a given image area in the frame acoustic line signal Bf in terms of signal intensity or luminance, the higher the similarity between the two image areas and the higher the correlation between the two image areas. In addition, in this case, the motion amount calculator 109 calculates a direction and an amount of movement of image signals for the subject in the target image area $A_{(i,j)}$ based on the positional relationship between the target image area $A_{(i,j)}$ and a comparison-target image area $B_{(i,j)}$, which is an image area in the comparison-target frame acoustic line signal Bf indicating high correlation with the target image area $A_{(i,j)}$.

Alternatively, the motion amount calculator 109 may perform the motion amount calculation through optical flow estimation. An optical flow is a vector indicating velocity between pixels of frames corresponding to different time points. In gradient-based optical flow estimation, an optical flow is detected by calculating, on the assumption that only a small change in luminance occurs at a local image area and that signal intensity (or luminance) remains the same before and after movement, the direction in which signal intensity (or luminance) changes between frames. Further, the optical flow so detected is used to detect the change in position of a feature point in an image.

Here, regardless of the method adopted for the calculation of motion amounts, the calculation of motion amounts need not be performed by using continuous frames, and may alternatively be performed by comparing frames generated at time points differing from one another by a certain amount of time.

The motion amount calculator 109 outputs the motion amount for the frame acoustic line signal that is the processing target to the target area setter 110.

(3) Target Area Setter 110

The target area setter 110 sets a target area Bx. The target area Bx is a virtual area for generating a sub-frame acoustic line signal. More specifically, in the present disclosure, the term "target area" is used to indicate a virtual area for generating a sub-frame acoustic line signal for one transmission event. Further, one acoustic line signal is generated for each measurement point Pij that is included in the target area Bx. In other words, the target area Bx is set for each given transmission event in order to specify ones of the measurement points for which acoustic line signals are to be generated in response to the transmission event.

Further, in the present disclosure, a sub-frame acoustic line signal is a group of a plurality of acoustic line signals that are generated from one transmission event. As already described above, in response to one transmission event, a plurality of acoustic line signals are generated, each for a different one of the measurement points included in the target area Bx. Further, a sub-frame is a unit corresponding to a group of signals which are acquired from one transmission event and each of which corresponds to a different one of the measurement points Pij that are included in the target area Bx for the transmission event. Thus, a combination of multiple sub-frames acquired at different time points equals one frame.

The target area setter 110 sets the target area Bx for a given transmission event based on information acquired from the transmission beam former 103 and a motion amount acquired from the motion amount calculator 109. The information acquired from the transmission beam former 103 indicates the position of the transmission aperture Tx for the transmission event.

Figure 5:
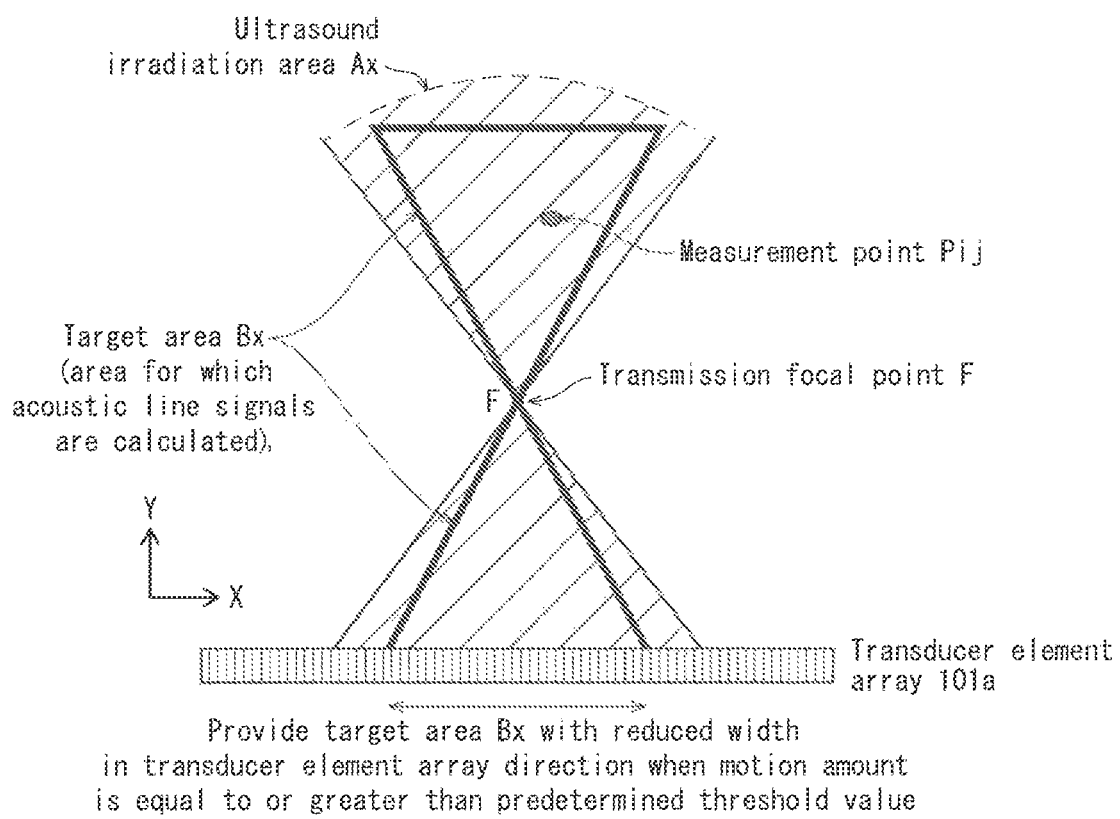
FIG. 5 is a schematic illustrating how a width of a target area Bx in a transducer element array direction is changed depending upon the motion amount.

FIG. 5 is a schematic illustrating how a width of the target area Bx in the transducer element array direction is changed depending upon the motion amount. As illustrated in FIG. 5, the target area Bx for a given transmission event is set within the ultrasound irradiation area Ax for the given transmission event. Further, the target area setter 110 reduces the width of the target area Bx when the motion amount is equal to or greater than a predetermined threshold value. Here, note that the user of the ultrasound diagnostic device 100 may set and change the predetermined threshold value as desired by performing user input.

The following explains why the width of the target area Bx in the transducer element array direction is reduced when the motion amount is equal to or greater than the predetermined threshold value. As described in detail later in the present disclosure, the synthesizer 1049 combines a plurality of sub-frame acoustic line signals to generate a frame acoustic line signal. Reducing the width of the target area Bx in the transducer element array direction reduces the number of acoustic line signals for the same measurement point that are included in different sub-frame acoustic line signals, which are combined with one another in the generation of the frame-acoustic line signal. Thus, reducing the width of the target area Bx in the transducer element array direction for a great motion amount (i.e., when the motion amount is equal to or greater than the predetermined threshold value) reduces the difference of the position of the subject, relative to reception transducer elements, between different sub-frame acoustic line signals combined to generate the frame acoustic line signal, and accordingly suppresses motion artifacts such as image blurs and false images occurring in response to movement.

Meanwhile, the target area setter 110 provides the target area Bx with increased width in the transducer element array direction when the motion amount is smaller than the predetermined threshold value. In the present embodiment, the length of the top edge and the bottom edge (i.e., the base) of the target area Bx, which has an hourglass shape, is reduced to a predetermined length when the motion amount is equal to or greater than the predetermined threshold value, and is increased slightly when the motion amount is smaller than the predetermined threshold value.

Providing the target area Bx with reduced width in the transducer element array direction when the motion amount is equal to or greater than the predetermined threshold value results in the size of the target area Bx being instantaneously reduced when the motion amount equals or exceeds the predetermined threshold value during ultrasound examination. This suppresses motion artifacts, such as image blurs and false images, appearing in an ultrasound image.

Meanwhile, providing the target area Bx with slightly greater width in the transducer element array direction when the motion amount is smaller than the predetermined threshold value prevents a rapid increase in the size of the target area Bx. This suppresses flickers appearing in ultrasound images.

The target area setter 110 may provide the target area Bx with the smallest possible width in the transducer element array direction when the motion amount is equal to or greater than a predetermined threshold value. In this case, the target area Bx, when having the smallest possible width, may be a straight line that passes through a center position of the transducer element array for the corresponding transmission event and that is perpendicular to the transducer element array. Alternatively, the target area Bx, when having the smallest possible width, may have a width in the transducer element array direction equal to a width of one transducer element residing at a center position of the transducer element array for the corresponding transmission event. This achieves instantaneously reducing the size of the target area Bx to as small a size as possible when the motion amount equals or exceeds the predetermined threshold value during ultrasound examination. This enhances the response of the motion artifact suppression effect, and contributes to an improvement in user convenience.

Alternatively, the target area setter 110 may provide the target area Bx with slightly smaller width when the motion amount is equal to or greater than the predetermined threshold value. This prevents a rapid decrease in the size of the target area Bx, and accordingly suppresses flickers appearing in ultrasound images.

Alternatively, the width of the target area Bx may be set based on multiple threshold values set with respect to the motion amount, in which case the width of the target area increases/decreases in multiple steps. This achieves even smoother and more detailed control, and achieves a desirable balance between the suppression of motion artifacts and the suppression of flickers.

In the present embodiment, the target area Bx is an hourglass-shaped area whose base is set along the subject surface that is in contact with the transmission transducer element array, and thus has a shape similar to the shape of the ultrasound irradiation area Ax. Providing the target area Bx with such a shape achieves distributing measurement points over substantially the entire ultrasound irradiation area Ax, which improves the efficiency of use of transmitted ultrasound.

However, the target area Bx may have a shape other than an hourglass shape. For example, in cases such as where the transducer elements belonging to the transmission transducer element array transmit parallel ultrasound waves, the target area Bx may be provided with a rectangular shape whose base is set along the subject surface that is in contact with the transmission transducer element array. Providing the target area Bx with such a shape results in measurement points being distributed over substantially the entire ultrasound irradiation area Ax, which improves the efficiency of use of transmitted ultrasound.

The target area setter 110 outputs the target area Bx set as above to the delay-and-sum calculator 1041.

(4) Delay-and-Sum Calculator 1041

Figure 6:
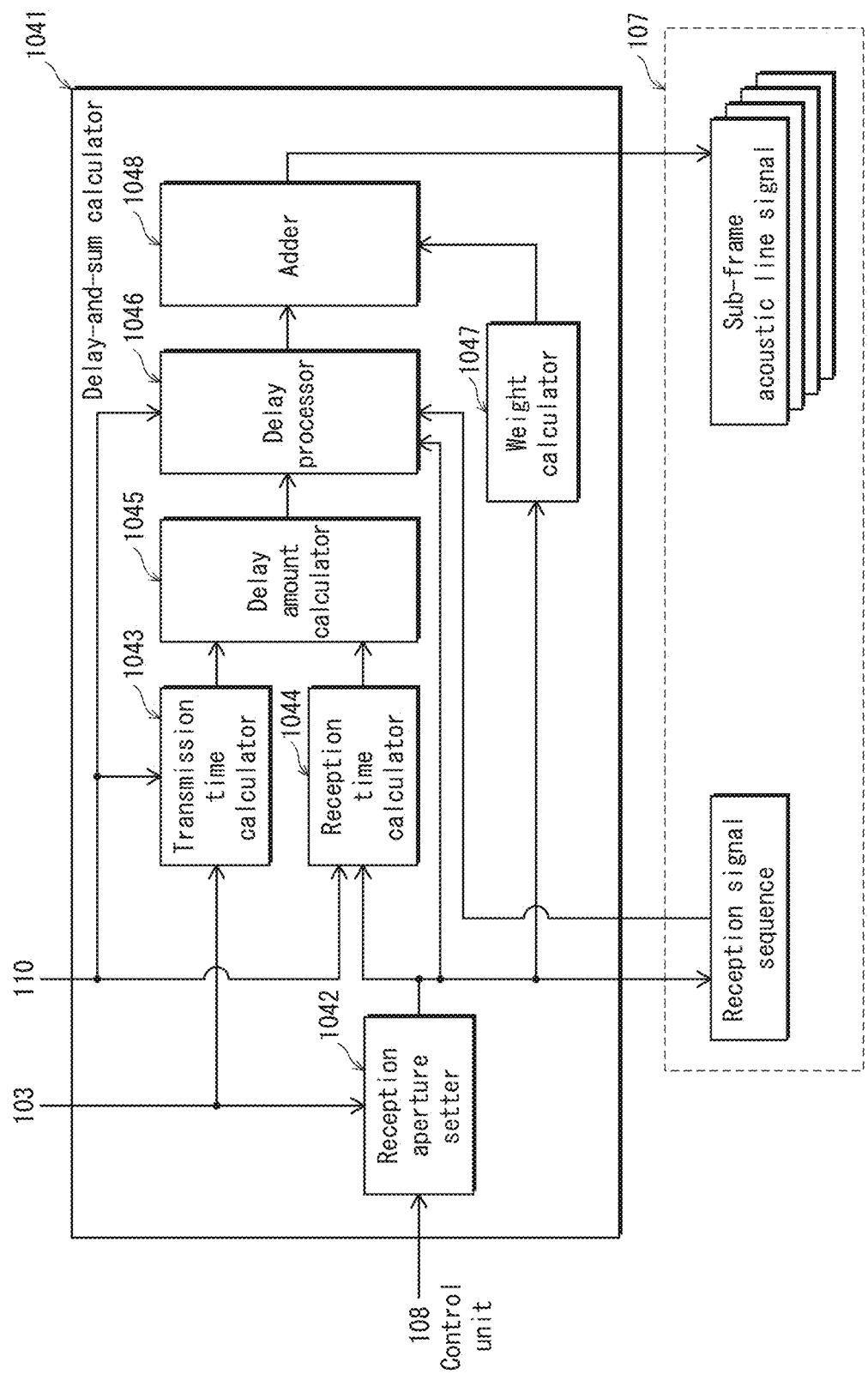
FIG. 6 is a functional block diagram illustrating the structure of a delay-and-sum calculator 1041.

The delay-and-sum calculator 1041 performs delay-and-sum processing with respect to reception signal sequences corresponding to the same measurement point P, each of which is received by one of the reception transducer elements Rk. The delay-and-sum calculator 1041 performs this processing for each measurement point Pij that is included in the target area Bx corresponding to a transmission event, and for each transmission event having been performed. The delay-and-sum calculator 1041, for each transmission event, generates a sub-frame acoustic line signal for the transmission event by calculating an acoustic line signal for each measurement point that is included in the target area Bx for the transmission event. FIG. 6 is a functional block diagram illustrating the structure of the delay-and-sum calculator 1041. As illustrated in FIG. 6, the delay-and-sum calculator 1041 includes: a reception aperture setter 1042; a transmission time calculator 1043; a reception time calculator 1044; a delay amount calculator 1045; a delay processor 1046; a weight calculator 1047; and an adder 1048.

The following describes the structure of each functional block of the delay-and-sum calculator 1041.

(i) Reception Aperture Setter 1042

The reception aperture setter 1042 is a circuit that sets, for each transmission event, a reception aperture Rx based on a control signal from the control unit 108 and information from the target area setter 110 indicating the target area Bx for the transmission event. In specific, for each measurement point P that is included in the target area Bx for the transmission event, the reception aperture setter 1042 selects some of the transducer elements 101a of the probe 101 as reception transducer elements (referred to in the following as a reception transducer element array) forming a reception aperture Rx whose center position corresponds to a transducer element that is spatially closest to the measurement point P.

Figure 7:
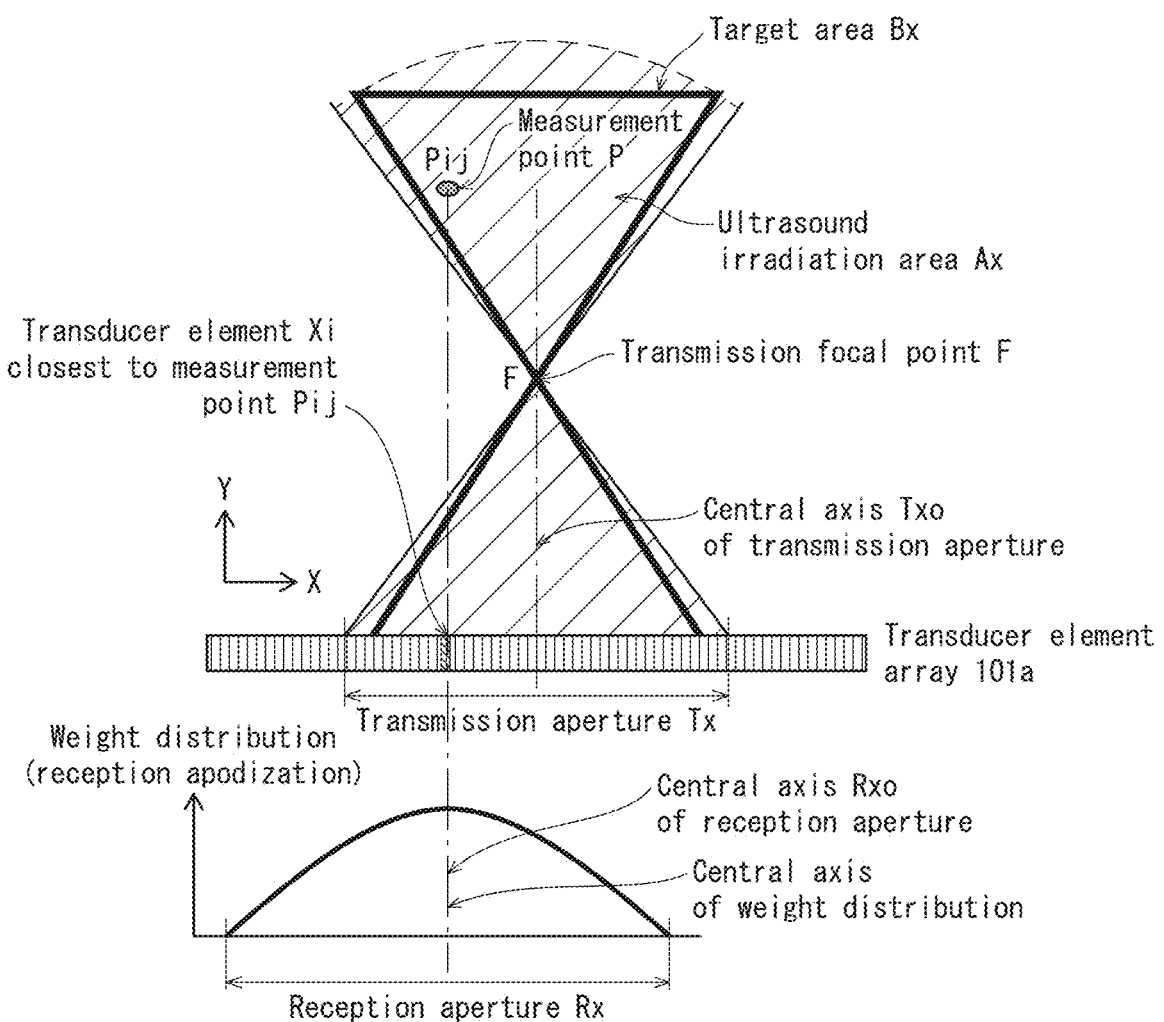
FIG. 7 is a schematic illustrating the relationship between a reception aperture Rx set by a reception aperture setter 1042 and a transmission aperture Tx.

The reception aperture setter 1042 sets, for each measurement point P that is included in the target area Bx for the transmission event, the reception aperture Rx (i.e., the reception transducer element array) so that the center position of the reception aperture Rx in the transducer element array direction corresponds to a transducer element that is spatially closest to the measurement point P. FIG. 7 is a schematic illustrating the relationship between the transmission aperture Tx for a given transmission event and a reception aperture Rx set by the reception beam former 104 for the transmission event. As illustrated in FIG. 7, for a given measurement point Pij, the reception aperture Rx is set so that the center position of the reception aperture Rx in the transducer element array direction corresponds to a transducer element Xk that is spatially closest to the measurement point Pij. Due to this, the position of the reception aperture Rx depends upon the position of the measurement point P, and does not change depending upon the position of the transmission aperture Tx, which shifts each time a transmission event is performed. That is, delay-and-sum processing for generating an acoustic line signal for a given measurement point Pij is always performed based on reception signal sequences acquired by reception transducer elements Rk composing the same reception aperture Rx. This means that with respect to the measurement point Pij, the same reception aperture Rx is used in delay-and-sum processing irrespective of transmission events.

In order to achieve utilizing reflected ultrasound from the entirety of the ultrasound irradiation area, the number of the reception transducer elements composing the reception aperture Rx for a given transmission event is, preferably, greater than or equal to the number of transmission transducer elements composing the transmission aperture Tx for the transmission event. For example, the number of reception transducer elements may be 32, 64, 96, 128, or 192.

The setting of the reception aperture Rx is performed for each transmission event. Due to this, the setting of the reception aperture Rx is repeated for the number of times transmission events are performed. Further, the setting of the reception aperture Rx may be performed each time a transmission event is performed as described above, or alternatively, reception apertures Rx for multiple transmission events having been performed may be set at once after the completion of the transmission events.

Further, the reception apparatus setter 1042 outputs information indicating the positions of the reception transducer elements composing the reception aperture Rx to the data storage 107, via the control unit 108.

The data storage 107 outputs the information indicating the positions of the reception transducer elements composing the reception aperture Rx along with reception signal sequences for the reception transducer elements to each of the transmission time calculator 1043, the reception time calculator 1044, the delay processor 1046, and the weight calculator 1047.

(ii) Transmission Time Calculator 1043

The transmission time calculator 1043 is a circuit that, for each transmission event, calculates a transmission time for each measurement point P that is included in the target area Bx for the transmission event. The transmission time is the amount of time required for transmitted ultrasound to arrive at each measurement point P. The transmission time calculator 1043 acquires information indicating the positions of the transmission transducer elements for a given transmission event from the data storage 107. In addition, the transmission time calculator 1043 acquires information indicating the position of the target area Bx for the transmission event in the ultrasound irradiation area Ax, from the target area setter 110. Based on both such information, the transmission time calculator 1043, for a measurement point Pij within the target area Bx, calculates the transmission time required for transmitted ultrasound to arrive at the measurement point Pij.

Figure 8:
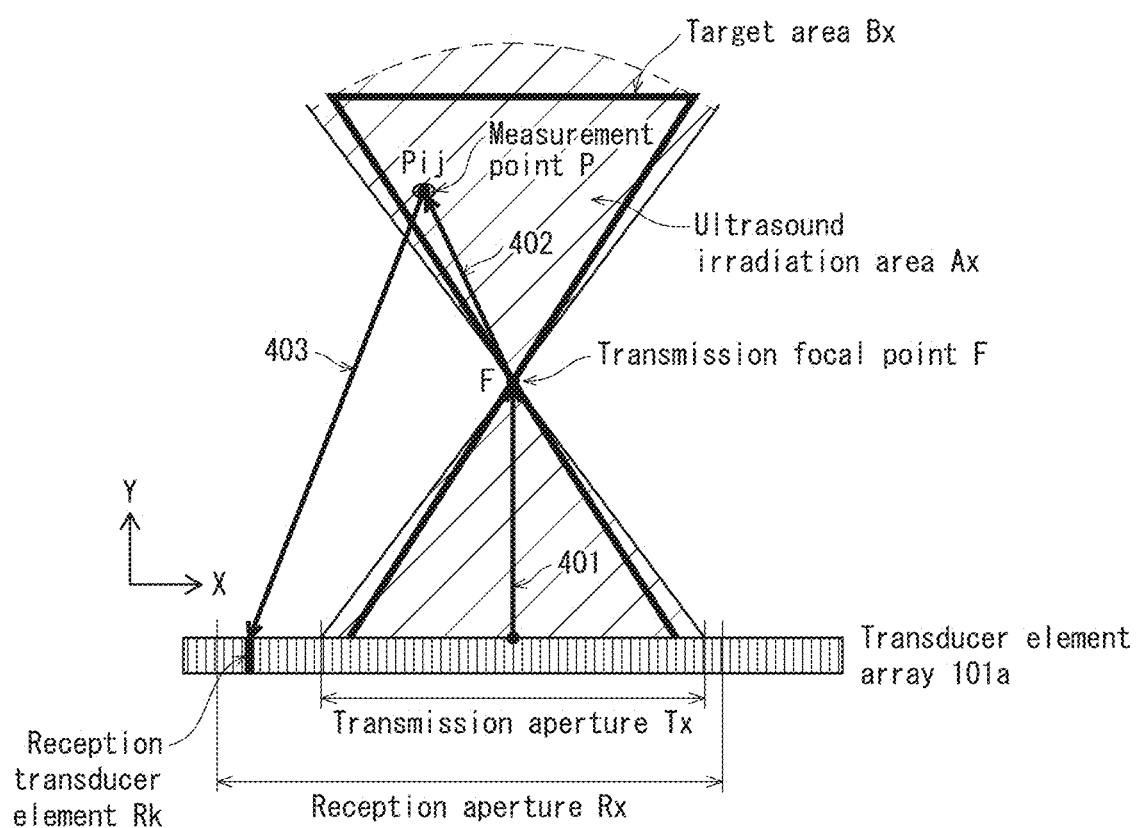
FIG. 8 is a schematic illustrating a propagation path of ultrasound that is transmitted from the transmission aperture Tx, is reflected at a measurement point Pij within the target area Bx, and arrives at a reception transducer element Rk included in the reception aperture Rx.

FIG. 8 is a schematic illustrating a propagation path of ultrasound that is transmitted from the transmission aperture Tx for a transmission event, is then reflected at a measurement point Pij that is included in the target area Bx for the transmission event, and finally arrives at a reception transducer element Rk of the reception aperture Rx.

Following emission of ultrasound from the transmission aperture Tx, the wavefront of the ultrasound converges at the transmission focal point F after proceeding along the path 401. Subsequently, the wavefront of the ultrasound expands and arrives at the measurement point Pij. When there is a change in acoustic impedance at the measurement point Pij, the transmitted ultrasound generates ultrasound reflection, which is received by the reception transducer element Rk of the reception aperture Rx. The transmission focal point F is preset in advance upon designing of the transmission beam former 103. Thus, the length of the path 402 from the transmission focal point F to the measurement point Pij can be calculated geometrically.

For each transmission event, the transmission time calculator 1043 calculates the transmission time for each measurement point Pij in the target area Bx for the transmission event. That is, the transmission time calculator 1043 calculates, for each measurement point Pij, the time required for transmitted ultrasound to arrive at the measurement point Pij. Further, the transmission time calculator 1043 outputs the transmission time so calculated to the delay amount calculator 1045.

(iii) Reception Time Calculator 1044

The reception time calculator 1044 is a circuit that calculates a reception time required for ultrasound reflection from each measurement point P to arrive at each reception transducer element Rk of the reception aperture Rx. For a given transmission event, the reception time calculator 1044 acquires information indicating the positions of the reception transducer elements Rk for the given transmission event from the data storage 107, and acquires the information indicating the position of the target area Bx for the given transmission event from the target area setter 110. Based on such information, the reception time calculator 1044, for a measurement point Pij in the target area Bx, calculates the reception time required for transmitted ultrasound to arrive at each reception transducer element Rk after being reflected at the measurement point Pij.

As already discussed above, transmitted ultrasound arriving at a measurement point Pij generates ultrasound reflection when there is a change in acoustic impedance at the measurement point Pij. The reflected ultrasound is then received by reception transducer elements Rk of the reception aperture Rx. As discussed above, the reception time calculator 1044 acquires the information indicating the positions of the reception transducer elements Rk of the reception aperture Rx from the data storage 107. Accordingly, the reception time calculator 1044 is able to geometrically calculate the length of the path 403 from the measurement point Pij to each of the reception transducer elements Rk.

For each transmission event, the reception time calculator 1044 calculates the reception time for each measurement point P that is included in the target area Bx. That is, the reception time calculator 1044 calculates, for each measurement point P, the time required for transmitted ultrasound to arrive at each reception transducer element Rk after being reflected at the measurement point P. Further, the reception time calculator 1044 outputs the reception time so calculated to the delay amount calculator 1045.

(iv) Delay Amount Calculator 1045

The delay amount calculator 1045 is a circuit that calculates, for each reception transducer element Rk, a total propagation time based on the transmission time and the reception time for the reception transducer element Rk. Further, the delay amount calculator 1045 calculates, for each reception transducer element Rk, a delay amount to be applied to a reception signal sequence for the reception transducer element Rk. In specific, the delay amount calculator 1045 acquires, from the transmission time calculator 1043, the transmission time required for ultrasound waves to arrive at a measurement point Pij. Further, for each reception transducer element Rk, the delay amount calculator 1045, acquires from the reception time calculator 1044, the reception time required for ultrasound to be reflected at the measurement point Pij and arrive at the reception transducer element Rk. Then, the delay amount calculator 1045, for each reception transducer element Rk, calculates a total propagation time required for transmitted ultrasound to arrive at the reception transducer element Rk. Further, based on the difference between total propagation times for the reception transducer elements Rk, calculates a delay amount for each reception transducer element Rk. For each measurement point P that is included in the target area Bx, the delay amount calculator 1045 calculates, for each reception transducer element Rk, the delay amount to be applied to a reception signal sequence for the reception transducer element Rk, and outputs the delay amounts to the delay processor 1046.

(v) Delay Processor 1046

The delay processor 1046 is a circuit that specifies, for each reception transducer element Rk, a reception signal based on reflected ultrasound from a measurement point Pij. In specific, for each reception transducer element Rk, the delay processor 1046 specifies a reception signal corresponding to the delay amount for the reception transducer element Rk from the reception signal sequence for the reception transducer element Rk.

More specifically, for each transmission event, the delay processor 1046 acquires, for each reception transducer element Rk, information indicating the position of the reception transducer element Rk from the reception aperture setter 1042, the reception signal sequence for the reception transducer element Rk from the data storage 107, and the delay amount to be applied to the reception signal sequence of the reception transducer element Rk from the delay amount calculator 1045. In addition, for each transmission event, the delay processor 1046 acquires the information indicating the position of the target area Bx from the target area setter 110. Further, for each reception transducer element Rk, the delay processor 1046 specifies a reception signal based on reflected ultrasound from a measurement point Pij. In specific, the delay processor 1046 specifies, from the reception signal sequence for the reception transducer element Rk, a reception signal corresponding to a time point after subtraction of the delay amount for the reception transducer element Rk.

(vi) Weight Calculator 1047

The weight calculator 1047 is a circuit that calculates a weight sequence (so-called reception apodization weight) for the reception transducer elements Rk, so that the maximum weight is set with respect to the reception transducer element located at the center position of the reception aperture Rx in the transducer element array direction.

As illustrated in FIG. 7, the weight sequence is a numerical sequence of weight coefficients that are to be applied to reception signals for the reception transducer elements composing the reception aperture Rx. The weight sequence indicates weights that are distributed symmetrically with respect to the transmission focal point F. As the shape of distribution of the weights indicated by the weight sequence, any shape is applicable, including but not limited to a hamming window, a hanning window, and a rectangular window. The weight sequence is set so that the maximum weight is set with respect to the reception transducer element located at the center position of the reception aperture Rx in the transducer element array direction, and the central axis of the weight distribution corresponds to the center axis Rxo of the reception aperture Rx. The weight calculator 1047 uses as input information indicating the positions of the reception transducer elements Rk, which is output from the reception aperture setter 1042, and outputs the weight sequence for the reception transducer elements Rk to the adder 1048.

(vii) Adder 1048

The adder 1048 is a circuit that generates an acoustic line signal for each measurement point P that is included in the target area Bx for a transmission event, by performing delay-and-sum processing using as input the specified reception signals for the reception transducer elements Rk, which are output from the delay processor 1046, and summing together the specified reception signals. Alternatively, the adder 1048 may generate an acoustic line signal for each measurement point P by using as input the weight numerical sequence for the reception transducer elements Rk, which is output from the weighting calculator 1047, multiplying the specified reception signal for each reception transducer element Rk by a corresponding weight, and summing the weighted reception signals. The adder 1048 sums the reception signals for the reception transducer elements Rk, after the reception signals have been put in the same phase by the delay processor 1046. Due to this, the adder 1048 is capable of increasing the S/N ratio of the reception signals received by the reception transducer elements Rk based on reflected ultrasound from the measurement point Pij, and reception signals for the measurement point Pij can be extracted.

As a result of one transmission event and processing accompanying the transmission event, an acoustic line signal is generated for each measurement point P in the target area Bx for the transmission event. Further, by repetitively performing transmission events while gradually shifting the transmission aperture Tx in the transducer element array direction each time, all of the transducer elements 101a in the probe 101 perform ultrasound transmission. Due to this, a frame acoustic line signal, which is a combination of acoustic line signals corresponding to one frame, is generated.

In the following, acoustic line signals for respective measurement points, which compose the frame acoustic line signal and each of which is generated by combining a plurality of acoustic line signals corresponding to the measurement point that are included in different sub-frame acoustic line signals, are each referred to as a combined acoustic line signal for the measurement point.

The adder 1048, for each transmission event, generates a sub-frame acoustic line signal being a combination of acoustic line signals for every measurement point Pij within the target area Bx for the transmission event. Further, the adder 1048 outputs the sub-frame acoustic line signals so generated to be stored in the data storage 107.

(5) Synthesizer 1049

Figure 9:
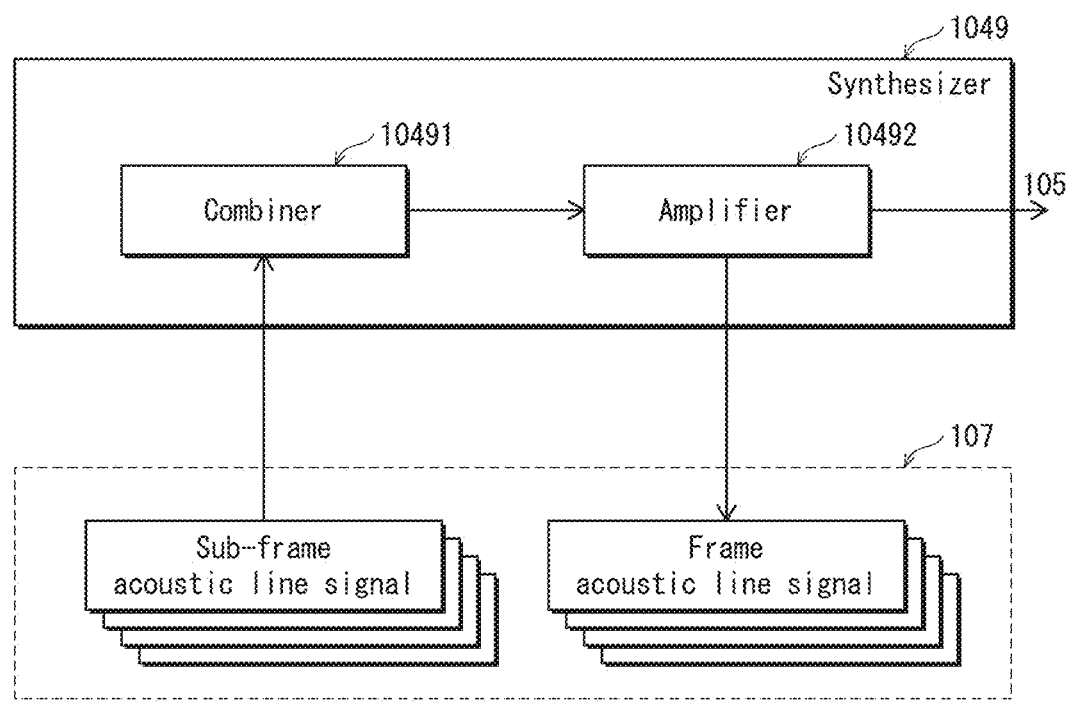
FIG. 9 is a functional block diagram illustrating the structure of a synthesizer 1049.

The synthesizer 1049 is a circuit that generates a frame acoustic line signal by combining a plurality of sub-frame acoustic line signals each generated for one transmission event. FIG. 9 is a functional block diagram illustrating the structure of the synthesizer 1049. As illustrated in FIG. 9, the synthesizer 1049 includes: a combiner 10491; and an amplifier 10492.

The following describes the structure of each functional block of the synthesizer 1049.

(i) Combiner 10491

The combiner 10491, after the generation of a series of sub-frame acoustic line signals necessary for generating one frame acoustic line signal is completed, reads out the sub-frame acoustic line signals from the data storage 107. Further, the combiner 10491 generates a frame acoustic line signal by combining the plurality of sub-frame acoustic line signals. The combining of the sub-frame acoustic line signals is performed according to the positions of the measurement points Pij, such that in the process, a combined acoustic line signal is generated for each measurement point Pij. In specific, the combiner 10491 generates a combined acoustic line signal for a given measurement point Pij by combining a plurality of acoustic line signals corresponding to the measurement point Pij that are included in different sub-frame acoustic line signals. Due to this, acoustic line signals for the same measurement point that are included in different sub-frame acoustic line signals are combined, to generate a combined acoustic line signal for the measurement point.

Figure 10:
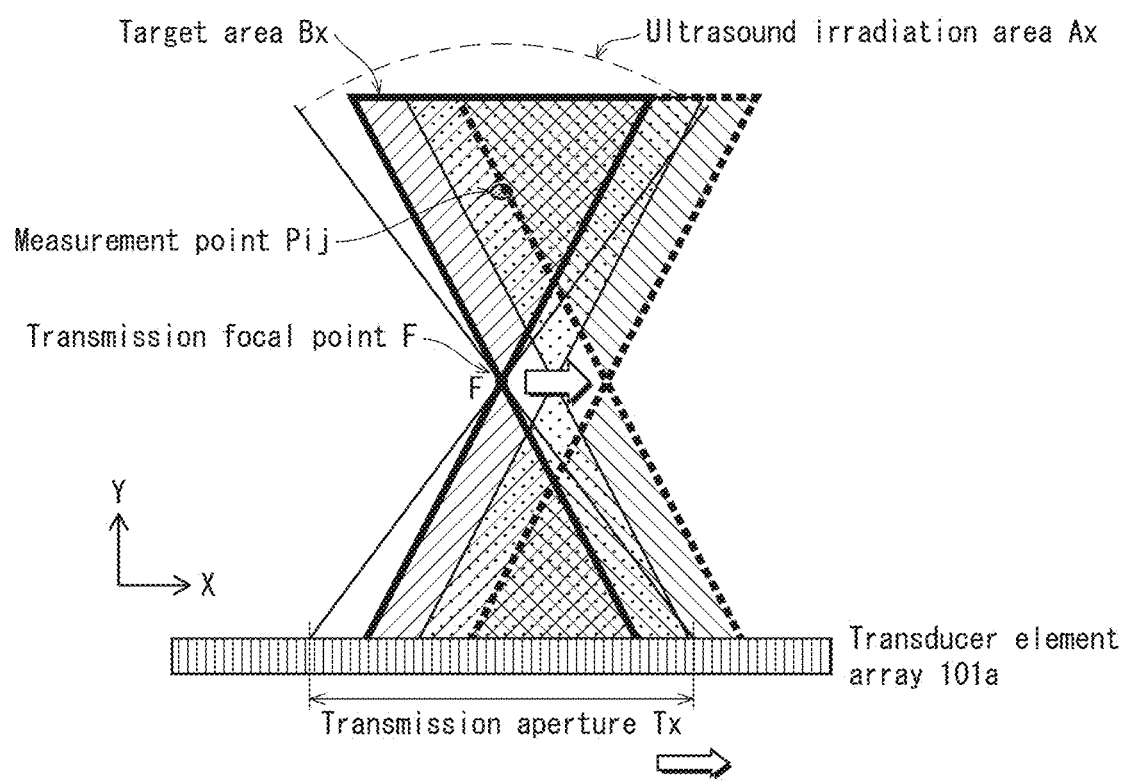
FIG. 10 is a schematic illustrating processing by a combiner 10491 for generating a combined acoustic line signal.

FIG. 10 is a schematic illustrating processing by the combiner 10491 for generating a combined acoustic line signal. As already discussed above, ultrasound transmission is performed by repetitively performing transmission events while gradually shifting the transmission transducer element array (i.e., the transmission aperture Tx) in the transducer element array direction each time. Due to this, the position of the target area Bx, which is set within the ultrasound irradiation area Ax of a corresponding transmission event, also shifts in the transducer element array direction from one transmission event to another. Thus, a frame acoustic line signal covering all measurement points can be generated by combining sub-frame acoustic line signals based on the positions of the measurement points Pij from which the acoustic lines signals included in the sub-frame acoustic line signals are acquired.

Further, for a measurement point included in multiple target areas Bx, values of a plurality of acoustic line signals included in different sub-frame acoustic line signals are summed. Thus, the combined acoustic line signal for such a measurement point may indicate a great value, depending upon the number of target areas Bx in which the measurement point is included. In the following, the number of different target areas Bx in which a given measurement point is included is referred to as an overlap count of the measurement point, and the maximum value of the overlap count in the transducer element array direction is referred to as a maximum overlap count.

Each of FIGS. 11A and 11B is a schematic illustrating the maximum overlap count for combined acoustic line signals, with FIG. 11A corresponding to a small motion amount and FIG. 11B corresponding to a great motion amount. As illustrated in FIG. 11A, the maximum overlap count is great for a small motion amount, reaching a maximum value pmax in this example. Meanwhile, the maximum overlap count is small for a great motion amount, not reaching the maximum value pmax and only reaching a value q smaller than pmax. The overlap count is small for a great motion amount since when the motion amount is great, the width of target area Bx in the transducer element array direction is reduced. Meanwhile, the overlap count is great for a small motion amount since when the motion amount is small, the width of target areas Bx in the transducer element array direction is increased. As such, combined acoustic line signals have different signal intensities, depending upon motion amount.

Further, in the present embodiment, the target area Bx has an hourglass-shape. Due to this, the overlap count and the maximum overlap count differ in the depth direction of the subject, as illustrated in FIGS. 11A and 11B. Accordingly, combined acoustic line signals for measurement points at different depths also have different values.

Note that in combining sub-frame acoustic line signals based on the positions of the measurement points Pij from which the acoustic lines line signals included in the sub-frame acoustic line signals are acquired to generate combined acoustic line signals for the respective measurement points, the combiner 10491 may add weights in accordance with the measurement points.

The combiner 10491 outputs the frame acoustic line signal so generated to the amplifier 10492.

(ii) Amplifier 10492

As already discussed above, values of combined acoustic line signals change depending upon motion amount. In addition, combined acoustic line signals also have different values in the depth direction. In order to moderate such variation between values of different combined acoustic line signals, the amplifier 10492, in combining the combined acoustic line signals to generate the frame acoustic line signal, performs amplification of multiplying the combined acoustic line signals by amplification factors. Here, the amplifier 10492 determines an amplification factor for a given combined acoustic line signal according to the number of acoustic line signals combined to yield the combined acoustic line signal.

Each of FIGS. 12A and 12B is a schematic providing an overview of the amplification performed by the amplifier 10492, with FIG. 12A corresponding to a small motion amount and FIG. 12B corresponding to a great motion amount. The maximum overlap count varies in the depth direction. Thus, to compensate with this variation in maximum overlap count, the amplifier 10492 multiplies the combined acoustic line signals by respective amplification factors that are based on the maximum overlap counts and vary in the depth direction, as illustrated in FIGS. 12A and 12B. Here, the amplification factors used by the amplifier 10492 are such that, the greater the width of the target area Bx in the transducer element array direction, the greater the difference between the amplification factors in the depth direction. This moderates a difference between values of combined acoustic line signals deriving from the difference in overlap counts in the depth direction, and thus, the values of the combined acoustic line signals after the amplification are averaged out in the depth direction. That is, the amplification performed by the amplifier 10492 is gain equalization in the depth direction.

Alternatively, the amplifier 10492 may also multiply the combined acoustic line signals by amplification factors varying in the transducer element array direction that are calculated based on overlap counts, when overlap counts vary in the transducer element array direction. This moderates a difference between values of combined acoustic line signals deriving from the difference in overlap counts in the transducer element array direction, and thus, the values of the combined acoustic line signals after the amplification are averaged out in the transducer element array direction.

Here, note that the amplifier 10492 may generate the frame acoustic line signal by combining amplified combined acoustic line signals for respective measurement points.

<Operations>

The following describes the operations of the ultrasound diagnostic device 100 having the structure described up to this point.

FIG. 13 is a flowchart illustrating beam forming by the reception beam former 104.

First, in Step S101, the transmitter 1031 performs transmission processing (a transmission event) of supplying a transmission signal causing transmission of an ultrasound beam to each transmission transducer element of the transmission aperture Tx.

In Step S102, the receiver 1040 generates reception signals based on electric signals yielded through the reception of reflected ultrasound by the probe 101, and outputs the reception signals to be stored in the data storage 107. Then, a determination is made of whether or not all transducer elements 101a of the probe 101 have performed ultrasound transmission (S103). When one or more of the transducer elements 101a have not yet performed ultrasound transmission, processing returns to Step S101, which results in another transmission event being executed by using the next transmission aperture Tx in the transducer element array direction. Meanwhile, when all of the transducer elements 101a have performed ultrasound transmission, processing proceeds to Step S201.

In Step S201, the motion amount calculator 109 calculates a motion amount based on a plurality of frame acoustic line signals stored in the data storage 107, and outputs the motion amount to the target area setter 110.

In Step S202, the target area setter 110 sets the target area Bx for an initial transmission event based on the position of the transmission aperture Tx for the initial transmission event and the motion amount. In the initial loop of processing, the target area setter 110 sets the target area Bx based on the ultrasound irradiation area Ax for the initial transmission event, which can be calculated from the transmission aperture Tx for the initial transmission event.

The following describes how the target area setter 110 sets the target area Bx for one transmission event (referred to in the following as a processing-target transmission event), which includes some of the measurement points Pij, in Step S202. FIG. 14 is a flowchart illustrating how the reception beam former 104 sets the target area Bx for the processing-target transmission event. First, the target area setter 110 acquires information indicating the position of the transmission aperture for the processing-target transmission event from the transmission beam former 103, and acquires the motion amount from the motion amount calculator 109 (Step S2021). The target area setter 110 judges whether the motion amount is equal to or greater than the predetermined threshold value (Step S2022). When the motion amount is equal to or greater than the predetermined threshold value, the target area setter 110 provides the target area Bx with, for example, minimum width in the transducer element array direction (Step S2023), and processing proceeds to Step S2027. Meanwhile, when the motion amount is smaller than the predetermined threshold value, the target area setter 110 judges whether the target area Bx already has a maximum width in the transducer element array direction (Step S2024). When the target area Bx already has the maximum width in the transducer element array direction, the target area setter 110 provides the target area Bx with the maximum width along the transmission element array direction (i.e., maintains the width of the target area Bx as it is) (Step S2025), and processing proceeds to Step S2027. When the target area Bx does not have the maximum width in the transducer element array direction, the target area setter 110 provides the target area Bx with slightly-increased width along the transmission element array direction (Step S2026), and processing proceeds to Step S2027. In Step S2027, the target area Bx so determined is output to the delay-and-sum calculator 1041.

Providing the target area Bx with the minimum width in the transducer element array direction when the motion amount is equal to or smaller than the predetermined threshold value achieves instantaneously reducing the size of the target area Bx when the motion amount is equal to or greater than the predetermined threshold value. Thus, this enhances the response of the motion artifact suppression effect of suppressing motion artifacts, such as image blurs and false images, in an ultrasound image.

Meanwhile, providing the target area Bx with slightly increased width in the transducer element array direction when the motion amount is smaller than the predetermined threshold value prevents a rapid increase in the size of the target area Bx. Thus, this suppresses flickers in ultrasound images.

Referring to FIG. 13 once again, the following describes measurement point-dependent beam forming (Step S20 (including Steps S204 through S211)). In Step S20, coordinate values i and j indicating a position of a measurement point Pij that is included in the target area Bx for the processing-target transmission event are initialized (set to the respective minimum possible values in the target area Bx for the processing-target transmission event) (Steps S205 and S206). Then, the reception aperture setter 1042 sets the reception aperture Rx for the current measurement point Pij so that the center position of the reception aperture Rx corresponds to a transducer element Xk that is spatially closest to the current measurement point Pij (Step S204).

Subsequently, an acoustic line signal is generated for the current measurement point Pij (Step S207).

The following describes the operations in Step S207 for generating an acoustic line signal for the current measurement point Pij. FIG. 15 is a flowchart illustrating the operations of the reception beam former 104 for generating the acoustic line signal for the current measurement point Pij. FIG. 16 is a schematic for explaining the operations of the reception beam former 104 for generating the acoustic line signal for the current measurement point Pij.

First, in Step S2071, the transmission time calculator 1043 calculates, for the current measurement point Pij, a transmission time required for transmitted ultrasound to arrive at the current measurement point Pij. As already described above, the current measurement point Pij is a measurement point included in the target area Bx for the processing-target transmission event. The transmission time can be calculated by dividing, by ultrasound velocity (cs), the geometrically-calculable length of the path (401+402) starting from a reception transducer element, passing through the transmission focal point F, and arriving at the current measurement point Pij.

Subsequently, value k, which indicates the position of a target reception transducer element Rk of the reception aperture Rx, is initialized (set to the minimum possible value in the reception aperture Rx) (Step S2072). Then, the reception time for the reception transducer element Rk is calculated (Step S2073). The reception time is the time required for transmitted ultrasound to arrive at the reception transducer element Rk after being reflected at the current measurement point Pij. The reception time for the reception transducer element Rk can be calculated by dividing, by ultrasound velocity (cs), the geometrically-calculable length of the path (403) starting from the current measurement point and arriving at the reception transducer element Rk. Further, from a sum of the transmission time and the reception time for the reception transducer element Rk, the total propagation time required for ultrasound transmitted from the transmission aperture Tx to arrive at the reception transducer element Rk after being reflected at the current measurement point Pij is calculated (Step S2074). Further, based on the difference in total propagation time between different reception transducer elements Rk, the delay amount for the reception transducer element Rk is calculated (Step S2075).

Subsequently, a determination is performed of whether or not a delay amount has been calculated for every reception transducer element Rk composing the reception aperture Rx (Step S2076). When a delay amount has not yet been calculated for one or more of the reception transducer elements Rk, the value k is incremented (Step S2077), and a delay amount for another reception transducer element Rk is calculated (Step S2073). Meanwhile, when a delay amount has been calculated for every reception transducer element Rk composing the reception aperture Rx, processing proceeds to Step S2078. Note that at this point, a delay amount with respect to the current measurement point Pij has already been calculated for each reception transducer element Rk of the reception aperture Rx. The delay amount for a given reception transducer element Rk indicates delay with which reflected ultrasound from the current measurement point Pij arrives at the reception transducer element Rk.

In Step S2078, the delay processor 1046, for each reception transducer element Rk, specifies a reception signal based on reflected ultrasound from the current measurement point Pij. Here, the delay processor 1046 specifies, from a reception signal sequence corresponding to the reception transducer element Rk, a reception signal corresponding to a time point after subtraction of the delay amount for the reception transducer element Rk.

Subsequently, the weight calculator 1047 calculates a weight sequence for the reception transducer elements Rk of the current reception aperture Rx, so that the maximum weight is set with respect to the reception transducer element located at the center position of the reception aperture Rx in the transducer element array direction (S2079). Then, the adder 1048 generates an acoustic line signal for the current measurement point Pij by multiplying the specified reception signal for each reception transducer element Rk by a weight corresponding to the reception transducer element Rk, and summing the weighted reception signals for the different reception transducer elements Rk (Step S2170). Following this, the adder 1048 outputs the acoustic line signal for the current measurement point Pij to the data storage 107 to be stored in the data storage 107 (Step S2171).

Referring to FIG. 13 once again, subsequently, an acoustic line signal is generated for each measurement point P (each illustrated in FIG. 16 as a black dot) that is included in the target area Bx for the processing-target transmission event by repeating Step S207 while incrementing the coordinate values i and j. Subsequently, a determination is performed of whether or not an acoustic line signal has been generated for every measurement point P that is included in the target area Bx for the processing-target transmission event (Steps S208 and S210). When an acoustic line signal has not yet been generated for one or more of the measurement points P that are included in the target area Bx, an acoustic line signal is generated for another measurement point Pij (Step S207) by incrementing the coordinate values i and j (Steps S209 and S211). Meanwhile, when an acoustic line signal has already been generated for each measurement point P that is included in the target area Bx, processing proceeds to Step S213. At this point, an acoustic line signal has already been generated for each measurement point P that is included in the target area Bx corresponding to the processing-target transmission event, and the acoustic line signals have been output to and stored to the data storage 107. In other words, a sub-frame acoustic line signal for the processing-target transmission event has been generated, and output to and stored to the data storage 107.

Subsequently, a determination is performed of whether or not a sub-frame acoustic line signal has been generated for each transmission event having been performed (Step S213). When sub-frame acoustic line signals have not yet been generated for one or more transmission events, processing proceeds to Step S205, where coordinate values i and j are initialized (set to the respective minimum possible values in the target area Bx for the subsequent transmission event, which can be calculated from the transmission aperture Tx for the subsequent transmission event) (Steps S205 and S206), and then setting of a reception aperture Rx is performed (Step S204). Meanwhile, when sub-frame acoustic line signals have been generated for every transmission event having been performed, processing proceeds to Step S301.

In Step S301, the combiner 10491 reads out the sub-frame acoustic line signals stored in the data storage 107, and combines the sub-frame acoustic line signals based on positions of the measurement points Pij. Thus, a combined acoustic line signal is generated for each measurement point Pij, and accordingly, a frame acoustic line signal is generated. Subsequently, the amplifier 10492 multiples each combined acoustic line signal by a corresponding amplification factor that is determined based on the number of acoustic line signals, included in the sub-frame acoustic line signals, that have been combined to yield the combined acoustic line signal (Step S302). Further, the amplifier 10492 outputs the amplified frame acoustic line signal to the ultrasound image generator 105 and the data storage 107 (Step S303), whereby processing is terminated.

<Evaluation of Improvement in Image Quality>
1. Motion Artifacts

In order to confirm the effects of the ultrasound diagnostic device 100 of improving image quality, evaluation was performed by causing B-mode images generated by the ultrasound image generator 105 based on frame acoustic line signals to be displayed on the display unit 106.

Through the evaluation, it was confirmed that the ultrasound diagnostic device 100 yields clear images with reduced image blurs, irrespective of whether the motion amount was great or small. Thus, it was confirmed that the ultrasound diagnostic device 100 yields high quality ultrasound images with high resolution, with low noise, and with reduced motion artifacts.

As discussed above, the target area setter 110 of the ultrasound diagnostic device 100 provides the target area Bx with reduced width in the transducer element array direction when the motion amount is equal to or greater than the predetermined threshold value. This reduces, for a given measurement point, the number of sub-frame acoustic line signals corresponding to the measurement point that the combiner 10491 uses to generate a combined acoustic line signal for the measurement point. As already described above, the combiner 10491 uses acoustic line signals corresponding to a same measurement point that are included in different sub-frame acoustic line signals for generating a combined acoustic line signal for the measurement point. Reducing the number of sub-frame acoustic line signals corresponding to a same measurement point combined for generating a combined acoustic line signal for the measurement point practically means that the combined acoustic line signal for the measurement point is generated based on a reduced number of transmission events.

As already discussed above, ultrasound transmission is performed by repetitively performing transmission events while gradually shifting the transmission aperture Tx in the transducer element array direction each time. Due to this, reducing the number of transmission events based on which a combined acoustic line signal is generated when the motion amount is relatively great suppresses the influence of the subject's movement, relative to the reception transducer elements, occurring between different transmission events. This reduces the influence of the subject having different positions relative to the reception transducer elements in different sub-frame acoustic line signals used to create the frame acoustic line signal, and thus suppresses motion artifacts caused by the displacement (movement) of the subject, such as image blurs and false images.

That is, the configuration of providing the target area Bx with reduced width in the transducer element array direction when the motion amount is equal to or greater than the predetermined threshold value suppresses motion artifacts, such as image blurs and false images, occurring as a result of the movement of the subject and the transducer elements relative to one another, such as the movement of the subject or the movement of the probe.

1. Effects of Amplification (Depth-Direction Gain Equalization for Reducing Unevenness in Depth Direction)

In order to confirm the effects of the ultrasound diagnostic device 100 of improving image quality through the amplification pertaining to the present embodiment, evaluation was performed of displayed B-mode images.

FIG. 17 includes photographs of B-mode images generated by the ultrasound diagnostic device 100 based on frame acoustic line signals. In each B-mode image, the horizontal direction corresponds to the transducer element array direction, and the vertical direction corresponds to the depth direction. Further, the numeric value TXAP at the top of each B-mode image is the width of the base of the target area Bx having the hourglass shape, expressed by using the number of transducer elements. Meanwhile, FIG. 18 includes photographs of B-mode images generated by the ultrasound diagnostic device 100 based on frame acoustic line signals generated without performing the amplification pertaining to the present embodiment.

In FIG. 18, particularly in B-mode images for smaller TXAP values, boundaries between areas with different image densities were prominent at multiple areas in the vertical direction (indicated by the arrows in FIG. 18). This shows that the greater the motion amount, the more prominent the boundaries between areas with different image density. These boundaries correspond to boundaries where the width of the target area Bx in the transducer element array direction changes along the depth direction. From this, it can be assumed that the luminance boundaries are the result of the width of the target area Bx in the transducer element array direction decreasing at such boundaries. By comparing FIG. 18 showing B-mode images without the amplification pertaining to the present embodiment and FIG. 17 illustrating B-mode images with the amplification pertaining to the present embodiment, it is clear that the ultrasound diagnostic device 100, by performing the amplification pertaining to the present embodiment, reduces the prominence of the image density boundaries in the depth direction, even when the motion amount is great.

<Effects>

As described above, the ultrasound diagnostic device 100 pertaining to the present embodiment, according to the synthetic aperture method, synthesizes acoustic line signals for the same measurement point that are generated in response to different transmission events. This achieves the effect of performing, for multiple transmission events, virtual transmission focusing even for measurement points that are located in depths other than that of the transmission focal point F. This improves spatial resolution and S/N ratio.

Further, the ultrasound diagnostic device 100 calculates a motion amount based on frame acoustic line signals, and performs a judgment based on the magnitude of the motion amount. Further, the ultrasound diagnostic device 100, when the motion amount is equal to or greater than a predetermined threshold value, provides the target area Bx with reduced width in the transducer element array direction, or more specifically, reduces the width of the target area Bx to a predetermined minimum width. As described above, the target area Bx for a transmission event is a virtual area for generating a sub-frame acoustic line signal for the transmission event. Due to this, the ultrasound diagnostic device 100 reduces the number of sub-frame acoustic line signals used for generating a frame acoustic line signal when the motion amount detected from frame acoustic line signals is equal to or greater than the predetermined threshold value. Thus, the ultrasound diagnostic device 100 is capable of suppressing the occurrence of motion artifacts such as image blurs and false images that result from movement in ultrasound images and are characteristic to the synthetic aperture method.

Further, the ultrasound diagnostic device 100 performs delaying based on the total propagation time, which is the time period from when ultrasound is transmitted from the transmission aperture Tx until the ultrasound is received by reception transducer elements Rk of the reception aperture Rx after passing through the transmission focal point F and being reflected at a measurement point P that is included in the target area Bx. This enables performing delay-and-sum processing focusing for each measurement point P that is included in the target area Bx, and generating an acoustic line signal for each measurement point P. This achieves generating, for one ultrasound transmission event, not only an acoustic line signal generated based on ultrasound reflection from an area of the ultrasound irradiation area along the central axis of the transmitted ultrasound beam, but also acoustic line signals generated based on ultrasound reflection from areas of the ultrasound irradiation area other than the rather narrow area along the central axis of the transmitted ultrasound beam, and thus, improves spatial resolution and signal S/N ratio by enhancing the efficiency of use of transmitted ultrasound.

In addition, in the ultrasound diagnostic device 100, the reception aperture setter 1042 sets, for each measurement point P, the reception aperture Rx so that the center position of the reception aperture Rx corresponds to a transducer element that is spatially closest to the measurement point P. Accordingly, reception beam forming is performed based on the position of the measurement point P rather than the corresponding transmission event, and by using a reception aperture that is symmetric about the measurement point P (i.e., has the same number of apertures at both sides of the center position thereof in the transducer element array direction). In addition, reception beam forming may be performed by using a reception apodization that has a symmetrical distribution at both sides of the measurement point P in the transducer element array direction. Due to this, the reception aperture (or the reception aperture and apodization weight) for a given measurement point does not change (i.e., the same reception aperture (or the same reception aperture and same apodization weight) is used for the same measurement point) between any transmission events, which involve shifting the transmission focal point F in the transducer element array direction. Thus, delay-and-sum processing for the same measurement point P is always performed by using the same reception aperture (or the same reception aperture and same apodization weight). In addition, in the ultrasound diagnostic device 100, a weight sequence is set so that the closer a reception transducer element is to the measurement point P, the greater the weight applied to the reception transducer element. Due to this, even taking into account the fact that ultrasound decay increases as propagation distance increases, ultrasound reflected from the measurement point P can be used with high efficiency. Accordingly, the ultrasound diagnostic device 100 achieves both high local spatial resolution and high S/N ratio.

Modification 1

The reception aperture setter 1042 in the ultrasound diagnostic device 100 pertaining to embodiment 1 sets, for each measurement point P, the reception aperture Rx so that the center position of the reception aperture Rx in the transducer element array direction corresponds to a transducer element that is spatially closest to the measurement point P. However, the configuration of the reception aperture Rx may be changed as necessary, as long as acoustic line signals for all measurement points P that are included in each target area Bx can be generated by calculating total propagation times and performing delaying based on total propagation paths. As already discussed above, a total propagation time for a given reception transducer element Rk is the time required for ultrasound transmitted from the transmission aperture Tx to reach the reception transducer element Rk after passing through the transmission focal point F and being reflected at the measurement point P.

The ultrasound diagnostic device pertaining to Modification 1 differs from the ultrasound diagnostic device 100 pertaining to embodiment 1 for including a reception aperture setter (a Tx reception aperture setter) that sets, for each transmission event, the reception aperture Rx so that the center position of the reception aperture Rx corresponds to the center position of the transmission aperture Tx for the transmission event. That is, the reception aperture Rx in modification 1 can be referred to as a transmission-dependent reception aperture. Other than the Tx reception aperture setter, the constituent elements of the ultrasound diagnostic device pertaining to modification 1 have the same structures and configurations as the corresponding constituent elements in the ultrasound diagnostic device 100 described in embodiment 1. Thus, description of such similar constituent elements is not provided in the following.

FIG. 19 is a schematic illustrating the relationship between the transmission aperture Tx for a given transmission event and the reception aperture Rx set by the Tx reception beam former for the transmission event. In modification 1, the Tx reception aperture setter sets, for each transmission event, the reception aperture Rx so that the center position of the reception aperture Rx in the transmission element array direction corresponds to the center position of the transmission aperture Tx for the transmission event. The position of an axis Rxo passing through the center position of the reception aperture Rx corresponds to the position of an axis Txo passing through the center position of the transmission aperture Tx. Further, the reception aperture Rx is symmetric about the transmission focal point F (i.e., has the same number of apertures at both sides of the center position thereof in the transmission array direction). As such, as the transmission aperture Tx shifts in the transducer element array direction from one transmission event to another, the reception aperture Rx also shifts in the transducer element array direction, following the transmission aperture Tx.

In addition, a weight sequence (so-called reception apodization weight) for the reception transducer elements Rk is calculated, so that the maximum weight is set with respect to the reception transducer element located along the center axis Rxo of the reception aperture Rx and the center axis Txo of the transmission aperture Tx. The weight sequence indicates weights distributed symmetrically with respect to a transmission transducer element located at the center position of the transmission aperture Tx. As the shape of distribution of the weights indicated by the weight sequence, any shape is applicable, including but not limited to a hamming window, a hanning window, and a rectangular window.

<Operations>

FIG. 20 is a flowchart illustrating the operations of a reception beam former of the ultrasound diagnostic device pertaining to modification 1 for beam forming. The flowchart in FIG. 20 differs from the flowchart in FIG. 13 for transmission-dependent dependent beam forming (Step S40 (including Steps S404 through S411)) being performed in place of measurement point-dependent beam forming (Step S20 (including Steps S204 through S211)). Meanwhile, the processing in steps other than Step S40 in the flowchart in FIG. 20 is similar to the processing in the corresponding steps in the flowchart in FIG. 13. Thus, description of such similar processing is not provided in the following.

In Step S40, first, the TX reception aperture setter sets a reception aperture Rx for a transmission event by selecting reception transducer elements Rk composing a reception element array whose center position matches the center position of the transducer element array for the corresponding transmission event, in Step S404.

Subsequently, coordinate values i and j indicating a position of a measurement point Pij that is included in the target area Bx for the processing-target transmission event are initialized (set to the respective minimum possible values in the target area Bx set in Step S202) (Steps S405 and S406). Subsequently, an acoustic line signal is generated for the current measurement point Pij (Step S407). FIG. 21 is a schematic for explaining the operations of the reception beam former pertaining to modification 1 for generating the acoustic line signal for the current measurement point Pij. FIG. 21 differs from FIG. 13 referred to in embodiment 1 in terms of the positional relationship between the transmission aperture Tx and the reception aperture Rx. The processing in Step S407 is similar to that in Step S207 of FIG. 13 (i.e., Steps S2071 through S2171 in FIG. 15).

An acoustic line signal is generated for each measurement point Pij (each illustrated in FIG. 21 as a black dot) that is included in the target area Bx by repeating Step S407 while incrementing the coordinate values i and j. Subsequently, a determination is performed of whether or not an acoustic line signal has been generated for every measurement point Pij that is included in the target area Bx (Steps S408 and S410). When an acoustic line signal has not yet been generated for one or more measurement points Pij that are included in the target area Bx, an acoustic line signal is generated for another measurement point Pij (Step S407) by incrementing the coordinate values i and j (Steps S409 and S411). Meanwhile, when an acoustic line signal has already been generated for each measurement point Pij that is included in the target area Bx, processing proceeds to Step S213. At this point, an acoustic line signal has already been generated for each measurement point P that is included in the target area Bx for the processing-target transmission event, and the acoustic line signals have been output to and stored to the data storage 107.

Subsequently, a determination is performed of whether or not a sub-frame acoustic line signal has been generated for each transmission event having been performed (Step S213). When sub-frame acoustic line signals have not yet been generated for one or more transmission events, processing proceeds to Step S202, where the target area Bx corresponding to the transmission aperture Tx for the subsequent transmission event is set, and then setting of a reception aperture Rx is performed (Step S404). Meanwhile, when sub-frame acoustic line signals have been generated for every transmission event having been performed, processing proceeds to Step S301.

Subsequently, a plurality of sub-frame acoustic line signals are combined based on positions of the measurement points Pij, and a frame acoustic line signal is generated (Step S301). Here, the frame acoustic line signal is composed of combined acoustic line signals for respective measurement points. Then, each combined acoustic line signal is multiplied by an amplification factor that is determined based on the number of acoustic line signals combined to yield the combined acoustic line signal (Step S302), before being output to the ultrasound image generator 105 and the data storage 107 (Step S303).

<Effects>

The ultrasound diagnostic device pertaining to modification 1, which has been described up to this point, achieves the effects described in embodiment 1, other than the effect related to setting a measurement point-dependent reception aperture. In place of the effect related to setting a measurement point-dependent reception aperture, the ultrasound diagnostic device pertaining to modification 1 achieves the following effect. In modification 1, for each transmission event, the reception aperture Rx is set by selecting reception transducer elements forming a transducer element array whose center position corresponds to the center position of the transducer element array for the transmission event. Due to this, the position of the central axis Rxo of the reception aperture Rx for a given transmission event corresponds to the position of the central axis Txo of the transmission aperture Tx for the same transmission event. Further, when transmission events are repetitively performed, the transmission aperture Tx shifts in the transducer element array direction each time, and the reception aperture Rx also shifts in the transducer element array direction in synchronization with the transmission aperture Tx. Thus, a different reception aperture (or a different reception aperture and different apodization weight) is used to perform delay-and-sum for each transmission event. Accordingly, reception processing with respect to multiple transmission events can be performed by using a group of reception apertures (or a group of reception apertures and apodization weights) covering a vast measurement area and each differing in terms of time. Thus, uniform spatial resolution is achieved over a vast measurement area.

Embodiment 2

In the ultrasound diagnostic device 100 pertaining to embodiment 1, the motion amount calculator 109 uses a plurality of frame acoustic line signals as input, and calculates a motion amount indicating the movement of image signals for the subject between the plurality of frame acoustic line signals by performing image analysis. However, as long as the motion amount calculator 109 is capable of detecting a motion amount indicating the movement of image signals for the subject based on reflected ultrasound, the motion amount calculator 109 need not perform image analysis on frame acoustic line signals, and may perform image analysis on other signals as appropriate.

Embodiment 2 describes an ultrasound diagnostic device that performs image analysis on sub-frame acoustic line signals to detect a motion amount. That is, the ultrasound diagnostic device pertaining to embodiment 2, for each transmission event, calculates a motion amount based on a plurality of sub-frame acoustic line signals each corresponding to one transmission event, and for each transmission event, sets the target area Bx so that the target area Bx reflects the motion amount detected based on the plurality of sub-frame acoustic line signals.

<Structure>

The following describes the ultrasound diagnostic device pertaining to embodiment 2, with reference to the accompanying drawings. FIG. 22 is a functional block diagram illustrating the structure of a reception beam former 104A of the ultrasound diagnostic device pertaining to embodiment 2. The ultrasound diagnostic device pertaining to embodiment 2 includes a motion amount calculator 109A. The motion amount calculator 109A, based on a plurality of sub-frame acoustic line signals stored in the data storage 107, calculates a motion amount indicating the movement of image signals for the subject between the sub-frame acoustic line signals. Note that each of the sub-frame acoustic line signals stored in the recording medium has been generated in response to one transmission event. In addition, the ultrasound diagnostic device pertaining to embodiment 2 includes a target area setter 110A that, for each transmission event, provides the target area Bx with reduced width in the transducer element array direction when the motion amount, detected for the transmission event, is equal to or greater than a predetermined threshold value. The ultrasound diagnostic device pertaining to embodiment 2 is characterized for including the motion amount calculator 109A and the target area setter 110A. Other than the motion amount calculator 109A and the target area setter 110A, the constituent elements of the ultrasound diagnostic device pertaining to embodiment 2 have the same structures and configurations as the corresponding constituent elements in the ultrasound diagnostic device 100 described in embodiment 1. Thus, description of such similar constituent elements is not provided in the following. That is, the ultrasound signal processing device of the ultrasound diagnostic device pertaining to embodiment 2 is constituted of an ultrasound signal processing circuit including, in addition to the reception aperture setter 1042, the multiplexer 102, the transmission beam former 103, and the ultrasound image generator 105.

(1) Motion Amount Calculator 109A

The motion amount calculator 109A performs image analysis on sub-frame acoustic line signals already stored in the data storage 107 to calculate a motion amount indicating the movement of image signals for the subject between the sub-frame acoustic line signals. The motion amount calculator 109A performs the calculation of motion amount for each transmission event. The motion amount calculator 109A calculates a motion amount from the sub-frame acoustic line signals by, for example, comparing the sub-frame acoustic line signals and calculating differences between corresponding image areas (composed of one or more pixels) of the sub-frame acoustic line signals, in terms of signal intensity, luminance, and/or the like. Here, it is preferable that sub-frame acoustic line signals used in motion amount calculation be sub-frame acoustic line signals that have been recently generated, among the sub-frame acoustic line signals stored in the data storage 107. For example, the motion amount calculator 109A may use two sub-frame acoustic line signals most recently generated for motion amount calculation, and compare a sub-frame acoustic line signal generated later among the two with a sub-frame acoustic line signal generated earlier among the two.

In embodiment 2, the motion amount calculator 109A acquires two sub-frame acoustic line signals from the data storage 107, and performs motion amount calculation by calculating a difference between the two sub-frame acoustic line signals, in terms of signal intensity or luminance. The motion amount calculator 109A calculates a motion amount in the same way as when the motion amount calculator 109 calculates a motion amount. Meanwhile, while the motion amount calculator 109 performs image analysis with respect to frame acoustic line signals in motion amount calculation as illustrated in FIG. 4, the motion amount calculator 109A performs image analysis with respect to sub-frame acoustic line signals.

For each transmission event, the motion amount calculator 109A outputs the motion amount calculated based on sub-frame acoustic line signals to the target area setter 110A.

Alternatively, instead of calculating the motion amount based on sub-frame acoustic line signals, the motion amount calculator 109A may calculate the motion amount based on reception signal sequences that have been generated based on reflected ultrasound in response to transmission events and that have not yet been delayed-and-summed.

(2) Target Area Setter 110A

The target area setter 110A, for each transmission event, sets the target area Bx based on information acquired from the transmission beam former 103 and a motion amount acquired from the motion amount calculator 109A. The information acquired from the transmission beam former 103 indicates the position of the transmission aperture Tx for the transmission event. The motion amount acquired from the motion amount calculator 109A, which is acquired for each transmission event, indicates the movement of image signals for the subject and is calculated based on sub-frame acoustic line signals. The target area setter 110A changes the width of the target area Bx in the same way as the target area setter 110 changes the width of the target area Bx in the transducer element array direction based on different motion amounts, which is illustrated in FIG. 5.

In the present embodiment, the target area setter 110A may provide the target area Bx with a minimum width in the transducer element array direction when the motion amount is equal to or greater than the predetermined threshold value.

The target area setter 110A outputs the target area Bx set as above to the delay-and-sum calculator 1041.

<Operations>

FIG. 23 is a flowchart illustrating beam forming by the reception beam former 104A. The flowchart in FIG. 23 differs from the flowchart in FIG. 13 for including Step S201A in place of Step S201 (motion amount calculation), and for including Step S202A in place of Step S202 (target area setting). Meanwhile, the processing in steps other than Steps S201A and 5202A in the flowchart in FIG. 23 is similar to the processing in the corresponding steps in the flowchart in FIG. 13. Thus, description of such similar processing is not provided in the following.

In Step S201A, the motion amount calculator 109A calculates a motion amount and outputs the motion amount to the target area setter 110A. The motion amount indicates the movement of image signals for the subject between sub-frame acoustic line signals stored in the data storage 107.

In Step S202A, the target area setter 110A sets the target area Bx for the processing-target transmission event based on information indicating the position of the transmission aperture Tx for the processing-target transmission event, which is acquired for the processing-target transmission event, and the motion amount, which is calculated for the processing-target transmission event based on sub-frame acoustic line signals.

In Step S202A, the target area setter 110A sets the target area Bx in the same way as illustrated in FIG. 14 (Steps S2021 through S2027). The target area setter 110A outputs the target area Bx determined as above to the delay-and-sum calculator 1041.

Subsequently, processing proceeds to measurement-point dependent beam forming (Step S20 (including Steps S204 through S211)). An acoustic line signal is generated for each measurement point Pij that is included in the target area Bx, by repeating Step S207 while incrementing the coordinate values i and j.

Subsequently, a determination is performed of whether or not a sub-frame acoustic line signal has been generated for each transmission event having been performed (Step S213). When sub-frame acoustic line signals have not yet been generated for one or more transmission events, processing returns to Step S202A, where the sub-frame acoustic line signals to be used for image analysis are updated, and motion amount calculation is performed based on a plurality of sub-frame acoustic line signals including the sub-frame acoustic line signal most recently generated. Further, the target area Bx for the subsequent transmission event is set in accordance with the motion amount so calculated and the position of the transmission aperture Tx for the subsequent transmission event (Step S202A), and the reception aperture Rx is set (Step S404). Meanwhile, when sub-frame acoustic line signals have been generated for all transmission events, processing proceeds to Step S301.

Subsequently, a plurality of sub-frame acoustic line signals are combined based on positions of the measurement points Pij, and a frame acoustic line signal is generated (Step S301). Here, the frame acoustic line signal is composed of combined acoustic line signals for respective measurement points. Then, each combined acoustic line signal is multiplied by an amplification factor that is determined based on the number of acoustic line signals combined to yield the combined acoustic line signal (Step S302), before being output to the ultrasound image generator 105 and the data storage 107 (Step S303).

<Effects>

As discussed up to this point, the ultrasound diagnostic device pertaining to embodiment 2 is similar to the ultrasound diagnostic device 100 pertaining to embodiment 1 for being capable of suppressing the occurrence of motion artifacts such as image blurs and false images that result from movement in ultrasound images and are characteristic to the synthetic aperture method, and thus yields high quality ultrasound images with high resolution, with low noise, and with reduced motion artifacts.

Further, the ultrasound diagnostic device pertaining to embodiment 2 calculates a motion amount for each transmission event, and performs a judgment based on the magnitude of the motion amount for each transmission event. Further, the ultrasound diagnostic device pertaining to embodiment 2, when the motion amount is equal to or greater than a predetermined threshold value, provides the target area Bx with a predetermined minimum width in the transducer element array direction. Accordingly, when a motion amount equal to or greater than the predetermined threshold value is calculated during the execution of a sequence of transmission events from which a frame acoustic line signal is to be generated, the ultrasound diagnostic device pertaining to embodiment 2 instantaneously reduces the size of the target area Bx. This enhances the motion artifact suppression effect of suppressing motion artifacts, such as image blurs and false images, in an ultrasound image.

Modification 2

The synthesizer 1049 of the reception beam former 104A of the ultrasound diagnostic device pertaining to embodiment 2, similar to that of the reception beam former 104 of the ultrasound diagnostic device 100, generates a frame acoustic line signal composed of combined acoustic line signals for respective measurement points by combining sub-frame acoustic line signals generated based on different transmission events. In specific, a combined acoustic line signal for a given measurement point is generated by combining acoustic line signals for the same measurement point that are included in the sub-frame acoustic line signals according to the positions of the measurement points from which the acoustic line signals have been acquired.

Meanwhile, modification 2 describes a reception beam former in which a synthesizer generates combined acoustic line signals in a manner different from the above, particularly when the target area setter 110A provides the target area for a given transmission event with reduced width in the transducer element array direction based on a determination that a motion amount acquired for the transmission event is equal to or greater than the predetermined threshold value. In specific, the synthesizer in the reception beam former pertaining to modification 2, when the target area setter 110A provides the target area for a given transmission event with reduced width in the transducer element array direction, sets zero as a value of each acoustic line signal in every sub-frame acoustic line signal acquired prior to the transmission event.

Further, the synthesizer of the reception beam former pertaining to modification 2 may generate a frame acoustic line signal composed of combined acoustic line signals for respective measurement points by combining sub-frame acoustic line signals generated based on different transmission events. In specific, a combined acoustic line signal for a given measurement point is generated by combining acoustic line signals for the same measurement point that are included in the sub-frame acoustic line signals according to the positions of the measurement points from which the acoustic line signals have been acquired.

Accordingly, even when the width of the target area Bx in the transducer element array direction is reduced due to a motion amount equal to or greater than the predetermined threshold value being calculated during the execution of a sequence of transmission events from which a frame acoustic line signal is to be generated, the occurrence of image unevenness (stripes) in B-mode images along the transducer element array direction, which would otherwise occur due to a change occurring in the number of sub-frame acoustic line signals being overlaid per measurement point, is suppressed, which results in the generation of ultrasound images without image unevenness.

Here, the target area setter 110A may provide the target area Bx with the minimum width in the transducer element array direction when the motion amount is equal to or greater than a predetermined threshold value.

Other Modifications

Up to this point, the technology pertaining to the present disclosure has been described based on specific embodiments and modifications thereof. However, the embodiments and modifications described above are non-limiting examples of application of the technology pertaining to the present disclosure, and thus, the technology pertaining to the present disclosure shall be construed to encompass the following exemplar modifications.

For example, the technology pertaining to the present disclosure may be implemented by using a computer system including a memory storing a computer program and a microprocessor operating based on the computer program. For example, the computer system may store a computer program of a diagnosis method of an ultrasound diagnostic device pertaining to the technology of the present disclosure, and the computer system may operate in accordance with the computer program or may provide instructions in accordance with the computer program to various components connected thereto.

Further, the technology pertaining to the present disclosure may be implemented by implementing a part of or the entirety of an ultrasound diagnostic device described above, or a part of or an entirety of an beam former described above by using a computer system including a microprocessor, a recording medium such as a ROM or a RAM, and a hard disk unit. In this implementation, a computer program achieving the same operations as a device described above is stored to the RAM or the hard disk unit. Further, in this implementation, various devices achieve their functions by the microprocessor operating in accordance with the computer program.

Further, the technology pertaining to the present disclosure may be implemented by implementing some or all constituent elements included in a device described above by using one system LSI (large scale integration). A system LSI is an ultra-multifunctional LSI manufactured by integrating multiple components onto one chip. Specifically, a system LSI is a computer system including a microprocessor, a ROM, a RAM, and the like. Further, each constituent element may be separately implemented by using one chip, or some or all constituent elements may be implemented by using one chip. Note that LSIs are referred to by using different names, depending upon the level of integration achieved thereby. Such names include IC, system LSI, super LSI, and ultra LSI. In this implementation, a computer program achieving the same operations as any device described above is stored to the RAM. Further, in this implementation, the system LSI achieves its functions by the microprocessor operating in accordance with the computer program. For example, the technology pertaining to the present disclosure encompasses a form of implementation where an LSI stores a beam forming method pertaining to the present disclosure as a program, the LSI is inserted into a computer, and the computer executes the program (i.e., the beam forming method pertaining to the present disclosure).

Note that integration of circuits may be achieved by a dedicated circuit or a general purpose processor, in addition to being achievable by using an LSI as discussed above. Further, a Field Programmable Gate Array (FPGA), which is programmable after manufacturing, or a reconfigurable processor, which allows reconfiguration of the connection and setting of circuit cells inside the LSI, may be used.

Furthermore, if technology for circuit integration that replaces LSIs emerges, owing to advances in semiconductor technology or to another derivative technology, the integration of functional blocks may naturally be accomplished using such technology.

Further, some or all functions of an ultrasound diagnostic device discussed in the embodiments may be implemented by a processor such as a CPU executing a program. Further, the technology pertaining to the present disclosure may be implemented by using a non-transitory computer-readable recording medium having recorded thereon a program causing execution of a diagnostic method and a beam forming method of an ultrasound diagnostic device. Further, execution of the program by another independent computer system may be achieved by transferring the program by recording the program or a signal onto a recording medium. Naturally, the program may be distributed via means of transmission media such as the internet.

Each of the ultrasound diagnostic devices pertaining to the embodiments includes the data storage, which is a recording device. However, the recording device need not be included in the ultrasound diagnostic devices, and may be implemented by using a semiconductor memory, a hard disk drive, an optical disk drive, a magnetic storage device, or the like connected to the ultrasound diagnostic devices from the outside.

Further, the functional blocks illustrated in the block diagrams are mere examples of possible functional blocks. That is, a plurality of functional blocks illustrated in the block diagrams may be combined to form one functional block, a given functional block illustrated in the block diagrams may be divided into a plurality of functional blocks, and a function of a given functional block illustrated in the block diagrams may be transferred to another functional block. Further, with regards to multiple functional blocks having similar functions, such functional blocks may be implemented by one piece of hardware or software executing such functions in parallel or by applying time division.

Further, the above-described order in which steps of processing are executed is a non-limiting example among multiple possible orders that is used for the sole sake of providing specific description of the technology pertaining to the present disclosure. Further, some of the steps of processing described above may be executed simultaneously (in parallel).

Further, in the embodiments, description is provided that the ultrasound diagnostic devices may have a probe and a display attached thereto. However, the ultrasound diagnostic devices may include a probe and a display therein.

Further, in the embodiments, the probe includes a plurality of piezoelectric transducer elements forming a line in one direction. However, the probe may have a different structure. For example, the probe may include a plurality of piezoelectric transducer elements disposed two-dimensionally. Alternatively, the probe may be a swingable probe including a plurality of swingable transducer elements (i.e., transducer elements that can be caused to swing by mechanical means) forming a line in one direction, which enables acquisition of three-dimensional tomographic images. Further, probes of different types may be selected and used depending upon the examination to be performed. For example, when using a probe including piezoelectric transducer elements disposed two-dimensionally, supplying different piezoelectric transducer elements with voltages at different timings or with voltages with different values achieves controlling the position, the direction, etc., of the ultrasound beam to be transmitted.

Further, the probe may be provided with some of the functions of the transmission beam former/reception beam former. For example, the probe may be capable of generating a transmission electric signal based on a control signal that the transmission beam former/reception beam former outputs to cause generation of a transmission electric signal, and of converting the transmission electronic signal into ultrasound. In addition, the probe may be capable of converting reflected ultrasound into a reception electric signal, and of generating a reception signal based on the reception electric signal.

Further, at least some of the functions of the ultrasound diagnostic devices pertaining to the embodiments and the modifications may be combined with functions of other ones of the ultrasound diagnostic devices pertaining to the embodiments and the modifications. Further, the values used above are non-limiting examples used for the sole sake of providing specific description of the technology pertaining to the present disclosure, and may be replaced with other values.

Further, the technology pertaining to the present disclosure should be construed as encompassing various modifications that a skilled artisan would arrive at based on the embodiments describe above.

CONCLUSION

As described above, one aspect of the present disclosure is an ultrasound signal processing device (i) performing a sequence of transmission events each involving selecting a first group of transducer elements from among a plurality of transducer elements of an ultrasound probe that are arranged in at least one line along a transducer element array direction, and causing each transducer element in the first group to transmit ultrasound towards a subject; (ii) for each of the transmission events, generating a sub-frame acoustic line signal based on ultrasound reflection received from the subject in response to the transmission event, to yield a plurality of sub-frame acoustic line signals each corresponding to a different one of the transmission events; and (iii) generating a frame acoustic line signal for the sequence based on the sub-frame acoustic line signals for the transmission events, the ultrasound signal processing device including ultrasound signal processing circuitry that operates as: a transmitter that, in each of the transmission events, selects the first group and causes each transducer element in the first group to transmit ultrasound towards the subject, the transmitter selecting the first group such that the first group shifts in the transducer element array direction from one transmission event to another; a receiver that, for each of the transmission events, selects a second group of transducer elements from among the plurality of transducer elements of the ultrasound probe, and generates a reception signal sequence for each transducer element in the second group based on ultrasound reflection received by the transducer element; a target area setter that, for each of the transmission events, sets a target area being a virtual signal area for generating the sub-frame acoustic line signal for the transmission event; a delay-and-sum calculator that, for each of the transmission events, generates the sub-frame acoustic line signal by performing, for each measurement point that is included in the target area for the transmission event, delay-and-sum processing with respect to one or more reception signal sequences generated based on ultrasound reflection received from the measurement point; and a synthesizer generating the frame acoustic line signal for the sequence based on the sub-frame acoustic line signals for the transmission events, and in the ultrasound signal processing device, the ultrasound signal processing circuitry further operates as a motion amount calculator that calculates, based on reflected ultrasound, a motion amount indicating movement between image signals for the subject, and the number of sub-frame acoustic line signals that the synthesizer uses to generate a frame acoustic line signal decreases when the motion amount is equal to or greater than a predetermined threshold.

This structure achieves generation of high quality ultrasound images with high resolution, with low noise, and with reduced motion artifacts.

In the ultrasound signal processing device pertaining to one aspect of the present disclosure, the target area setter may provide the target area with reduced width in the transducer element array direction when the motion amount is equal to or greater than the predetermined threshold.

This reduces, with a simple structure, the number of sub-frame acoustic line signals combined for generating a combined acoustic line signal, included in the frame acoustic line signal, that corresponds to one measurement point when the motion amount detected from reflected ultrasound is equal to or greater than the predetermined threshold. Thus, this structure suppresses the occurrence of motion artifacts such as image blurs and false images that result from movement in ultrasound images and are characteristic to the synthetic aperture method.

In the ultrasound signal processing device pertaining to one aspect of the present disclosure, the sub-frame acoustic line signals, each of which corresponding to one of the transmission events, may each include acoustic line signals for measurement points that are included in the target area for the corresponding transmission event, and the synthesizer may generate the frame acoustic line signal by combining the sub-frame acoustic signals based on positions of measurement points from which the acoustic line signals included in the sub-frame acoustic line signals are acquired.

This achieves, with a simple structure, an ultrasound signal processing device capable of generating high quality ultrasound images with high resolution, with low noise, and with reduced motion artifacts.

In the ultrasound signal processing device pertaining to one aspect of the present disclosure, the motion amount calculator may calculate the motion amount based on a plurality of frame acoustic line signals that have been generated in the past and are stored in a recording medium.

This reduces the number of sub-frame acoustic line signals combined for generating the frame acoustic line signal when the motion amount detected from reflected ultrasound is equal to or greater than the predetermined threshold. Thus, this structure suppresses the occurrence of motion artifacts such as image blurs and false images that result from movement in ultrasound images and are characteristic to the synthetic aperture method.

In the ultrasound signal processing device pertaining to one aspect of the present disclosure, the motion amount calculator may calculate the motion amount based on a difference between values of acoustic line signals corresponding to a same measurement point that are included in the frame acoustic line signals stored in the recording medium.

This achieves, with a simple structure, detecting a motion amount indicating the movement of image signals for the subject between frame acoustic line signals.

In the ultrasound signal processing device pertaining to one aspect of the present disclosure, the sub-frame acoustic line signals, from which the frame acoustic line signal is generated, may be generated based on the same target area.

This structure, even when the width of the target area Bx in the transducer element array direction is reduced due to a change in motion amount being detected during the execution of a sequence of transmission events from which a frame acoustic line signal is to be generated, suppresses the occurrence of image unevenness (stripes) in B-mode images along the transducer element array direction, which would otherwise occur due to a change occurring in the number of sub-frame acoustic line signals being overlaid per measurement point, is suppressed. Thus, this structure achieves the generation of ultrasound images without image unevenness.

In the ultrasound signal processing device pertaining to one aspect of the present disclosure, the motion amount calculator may calculate the motion amount based on a plurality of sub-frame acoustic line signals that have been generated in the past and are stored in a recording medium, and the target area setter may provide the target area for one transmission event with reduced width in the transducer element array direction compared to the target area for a previous transmission event when the motion amount is equal to or greater than the predetermined threshold.

This structure, when a motion amount equal to or greater than the predetermined threshold value is calculated during the execution of a sequence of transmission events from which a frame acoustic line signal is to be generated, instantaneously reduces the size of the target area Bx. This enhances the motion artifact suppression effect of suppressing motion artifacts, such as image blurs and false images, in an ultrasound image.

In the ultrasound signal processing device pertaining to one aspect of the present disclosure, the motion amount calculator may calculate the motion amount based on a difference between values of acoustic line signals corresponding to a same measurement point that are included in the sub-frame acoustic line signals stored in the recording medium.

This achieves, with a simple structure, detecting a motion amount indicating the movement of image signals for the subject between sub-frame acoustic line signals.

In the ultrasound signal processing device pertaining to one aspect of the present disclosure, when the target area setter provides the target area for the one transmission event with reduced width in the transducer element array direction compared to the target area for the previous transmission event, in the generation of the frame acoustic line signal, the synthesizer may set zero as a value of sub-frame acoustic line signals for ones of the transmission events prior to the one transmission event.

Further, in the ultrasound signal processing device pertaining to one aspect of the present disclosure, the sub-frame acoustic line signals, each of which corresponding to one of the transmission events, may each include acoustic line signals for measurement points that are included in the target area for the corresponding transmission event, and the synthesizer may generate the frame acoustic line signal by combining the sub-frame acoustic signals based on positions of measurement points from which the acoustic line signals included in the sub-frame acoustic line signals are acquired.

These structures, even when the width of the target area Bx in the transducer element array direction is reduced due to a change in motion amount being detected during the execution of a sequence of transmission events from which a frame acoustic line signal is to be generated, suppress the occurrence of image unevenness (stripes) in B-mode images along the transducer element array direction, which would otherwise occur due to a change occurring in the number of sub-frame acoustic line signals being overlaid per measurement point, is suppressed. Thus, these structures achieve the generation of ultrasound images without image unevenness.

In the ultrasound signal processing device pertaining to one aspect of the present disclosure, the synthesizer may generate the frame acoustic line signal by combining acoustic line signals corresponding to a same measurement point that are included in the sub-frame acoustic line signals.

This structure achieves the effect of performing, for multiple transmission events, virtual transmission focusing even for measurement points P that are located in depths other than that of the transmission focal point F. This improves spatial resolution and S/N ratio.

In the ultrasound signal processing device pertaining to one aspect of the present disclosure, the target area setter may provide the target area with minimum width in the transducer element array direction when the motion amount is equal to or greater than the predetermined threshold.

This structure, when a motion amount equal to or greater than the predetermined threshold value is calculated during ultrasound examination, instantaneously reduces the size of the target area Bx. This enhances the motion artifact suppression effect of suppressing motion artifacts, such as image blurs and false images, in an ultrasound image, and contributes to an improvement in user convenience.

In the ultrasound signal processing device pertaining to one aspect of the present disclosure, the target area setter may provide the target area for one transmission event with increased width in the transducer element array direction when the motion amount is smaller than the predetermined threshold, provided that the target area for a previous transmission event does not have maximum width in the transducer element array direction.

Further, in the ultrasound signal processing device pertaining to one aspect of the present disclosure, the target area setter may provide the target area with maximum width in the transmission array direction when the motion amount is smaller than the predetermined threshold, provided that the target area set for a previous transmission event has the maximum width in the transducer element array direction.

These structures suppress flickering in ultrasound images, for preventing a rapid increase in the size of the target area Bx.

In the ultrasound signal processing device pertaining to one aspect of the present disclosure, the target area setter may set the target area so as to be linear in shape, to be perpendicular to the transducer element array direction, and to pass through a center position of the first group in the transducer element array direction when the motion amount is equal to or greater than the predetermined threshold.

This structure suppresses the occurrence of motion artifacts such as image blurs and false images that result from movement in ultrasound images and are characteristic to the synthetic aperture method, which otherwise occur due to the overlaying of sub-frame acoustic line signals.

In the ultrasound signal processing device pertaining to one aspect of the present disclosure, the greater the motion amount may be, the smaller the number of acoustic line signals corresponding to a same measurement point that are included in the sub-frame acoustic line signals may be.

This structure suppresses the occurrence of motion artifacts characteristic to the synthetic aperture method.

In the ultrasound signal processing device pertaining to one aspect of the present disclosure, the frame acoustic line signal may be composed of a plurality of combined acoustic line signals, each of the combined acoustic line signals generated by combining ones of the acoustic line signals corresponding to a same measurement point that are included in the sub-frame acoustic line signals, and the ultrasound signal processing circuitry may further operate as an amplifier that multiplies each of the combined acoustic line signals by an amplification factor determined based on the number of acoustic line signals having been combined to yield the combined acoustic line signal.

Further, in the ultrasound signal processing device pertaining to one aspect of the present disclosure, the target area may have an hourglass shape, and a base of the target area may be along a surface of the subject that comes in contact with the first group, and different amplification factors may be used for different depths in the subject.

Further, in the ultrasound signal processing device pertaining to one aspect of the present disclosure, the greater the width of the target area in the transducer element array direction may be, the greater the difference between different amplification factors used for different depths in the subject may be.

This structure suppresses a difference between combined acoustic line signals deriving from the difference in overlap count depending upon the position in the depth direction, and thus, the values of the combined acoustic line signals after the amplification are averaged out in the depth direction. Further, this structure, due to the amplification being performed, reduces the prominence of image density boundaries in the depth direction, even when the motion amount is great.

In the ultrasound signal processing device pertaining to one aspect of the present disclosure, for each of the transmission events, the delay-and-sum processing may be performed by using reception signal sequences acquired from an array of transducer elements whose center position corresponds to a center position of the first group for the transmission event.

Thus, a different reception aperture is used to perform delay-and-sum for each transmission event. Accordingly, reception processing with respect to multiple transmission events can be performed by using a group of reception apertures covering a vast measurement area and each differing in terms of time. Thus, uniform spatial resolution is achieved over a vast measurement area.

In the ultrasound signal processing device pertaining to one aspect of the present disclosure, the delay-and-sum processing for each measurement point may be performed by using reception signal sequences acquired from an array of transducer elements whose center position corresponds to one of the plurality of transducer elements that is spatially closest to the measurement point.

This structure achieves using the same reception aperture for a given measurement point (i.e., the same reception aperture is used for the same measurement point) irrespective of transmission events, which involve shifting the transmission focal point F in the transducer array direction. Thus, delay-and-sum processing for the same measurement point P is always performed by using the same reception aperture. Accordingly, this structure achieves both high local spatial resolution and high S/N ratio.

In the ultrasound signal processing device pertaining to one aspect of the present disclosure, the ultrasound signal processing circuitry may further operates as a weight calculator that calculates a weight sequence to be applied to an array of transducer elements from which the reception signal sequences with respect to which the delay-and-sum calculator performs the delay-and-sum processing are acquired, the weight sequence including the greatest weight for a transducer element located at a center position of the array of transducer elements, and in the delay-and-sum processing for each measurement point, the delay-and-sum calculator, for each transducer element in the array of transducer elements, may specify a reception signal value corresponding to the measurement point and multiply the specified reception signal value by a corresponding weight included in the weight sequence.

This structure achieves setting a weight sequence so that that the closer a reception transducer is to the center of the reception aperture, the greater the weight applied to the reception transducer. Thus, this structure improves the sensitivity in receiving reflected ultrasound.

One aspect of the present disclosure is an ultrasound diagnostic device including the ultrasound signal processing device pertaining to one aspect of the present disclosure, and in the ultrasound diagnostic device, the ultrasound signal processing device is configured so that the ultrasound probe is connectable thereto.

This structure achieves an ultrasound diagnostic device capable of generating high quality ultrasound images with high resolution, with low noise, and with reduced motion artifacts.

In another aspect of the present disclosure, the delay-and-sum calculator may generate an acoustic line signal for a measurement point based on a total propagation time being an amount of time required for transmitted ultrasound to arrive at a reception transducer after being reflected at the measurement point.

This structure achieves a delay-and-sum calculator with a simple structure.

<<Supplement>>

Each of the embodiments described above should be construed as being a preferable and specific example of implementation of the technology pertaining to the present disclosure. As such, any value, any shape, any material, any constituent element, any position of any constituent element, any connection of any constituent element, any step, and any order in which any step is performed shall be construed as being a non-limiting example. Further, among the constituent elements described in the embodiments, any constituent element not recited in the independent claims, which represent the broadest concept of the present disclosure, shall be construed as a constituent element not necessarily essential but included in a preferable form of implementation of the technology pertaining to the present disclosure.

Further, in order to facilitate understanding, constituent elements described in the embodiments may be illustrated in drawings at a scale differing from their actual sizes. Further, the technology pertaining to the present disclosure shall not be construed as being limited to the embodiments, and instead, shall be construed as encompassing any modification that does not depart from the spirit and the scope of the present disclosure.

Further, the embodiments and modifications do not provide description of circuit parts and lead wires disposed on substrates in ultrasound diagnostic devices. This is since various forms of electric wiring and electric circuitry are implementable based on knowledge possessed by a skilled artisan in the present field of technology, and are not directly essential in describing the technology pertaining to the present disclosure. Further, all drawings referred to in the above are schematic drawings and may not be accurate in a strict sense.

Although the present invention has been fully described by way of examples with reference to the accompanying drawings, it is to be noted that various changes and modifications will be apparent to those skilled in the art. Therefore, unless such changes and modifications depart from the scope of the present invention, they should be construed as being included therein.

What is claimed is:

1. An ultrasound signal processing device
   (i) performing a sequence of transmission events each involving selecting a first group of transducer elements from among a plurality of transducer elements of an ultrasound probe that are arranged in at least one line along a transducer element array direction, and causing each transducer element in the first group of transducer elements to transmit ultrasound towards a subject;
   (ii) for each of the transmission events, generating a sub-frame acoustic line signal based on ultrasound reflection received from the subject in response to the transmission event, to yield a plurality of sub-frame acoustic line signals each corresponding to a different one of the transmission events; and (iii) generating a frame acoustic line signal for the sequence based on the sub-frame acoustic line signals for the transmission events, the ultrasound signal processing device comprising ultrasound signal processing circuitry that operates as:

a transmitter that, in each of the transmission events, selects the first group of transducer elements and causes each transducer element in the first group of transducer elements to transmit ultrasound towards the subject, the transmitter selecting the first group of transducer elements such that the first group of transducer elements shifts in the transducer element array direction from one transmission event to another, the first group of transducer elements forming a transmission aperture of each of the transmission events, the transmission aperture transmitting ultrasound in an ultrasound irradiation area for each of the transmission events;

a receiver that, for each of the transmission events, selects a second group of transducer elements from among the plurality of transducer elements of the ultrasound probe, and generates a reception signal sequence for each transducer element in the second group of transducer elements based on ultrasound reflection received by the transducer element;

a target area setter that, for each of the transmission events, sets a target area, wherein the target area is a virtual signal area having a width defined between two lateral borders within the ultrasound irradiation area irradiated by the transmission aperture of the each of the transmission events;

a delay-and-sum calculator that generates a plurality of acoustic line signals, each for a different one of measurement points included in the target area, for the each of the transmission events, the measurement points being defined by two coordinate values in the target area and the plurality of acoustic line signals are generated for the measurement points by incrementing one coordinate value at a time until all the measurement points in the target area for a transmission event have been processed, and the delay-and-sum calculator generates the sub-frame acoustic line signal within the target area for the each of the transmission events that includes the plurality of acoustic line signals for the each of the transmission events by performing, for each measurement point that is included in the target area for the transmission event, delay-and-sum processing with respect to one or more reception signal sequences generated based on ultrasound reflection received from the measurement point, and a size of the first group of transducer elements of the transmission aperture is maintained constant as the first group of transducer elements shifts in the transducer element array direction from one transmission event to another; and a synthesizer generating the frame acoustic line signal for the sequence based on the sub-frame acoustic line signals for the transmission events, wherein the ultrasound signal processing circuitry further operates as a motion amount calculator that calculates, based on reflected ultrasound, a motion amount indicating movement between image signals for the subject, and when the motion amount is equal to or greater than a predetermined threshold, the target area setter sets the target area smaller than the ultrasound irradiation area and provides the target area with a width between the lateral borders that is shorter in the transducer element array direction than when the motion amount is less than the predetermined threshold so that a number of the acoustic line signals generated for the each of the transmission events decreases.

2. The ultrasound signal processing device of claim 1, wherein the sub-frame acoustic line signals, each of which corresponding to one of the transmission events, each include the acoustic line signals for measurement points that are included in the target area for the corresponding transmission event, and the synthesizer generates the frame acoustic line signal by combining the sub-frame acoustic signals based on positions of measurement points from which the acoustic line signals included in the sub-frame acoustic line signals are acquired.

3. The ultrasound signal processing device of claim 1, wherein the motion amount calculator calculates the motion amount based on a plurality of frame acoustic line signals that have been generated in the past and are stored in a recording medium.

4. The ultrasound signal processing device of claim 3, wherein the motion amount calculator calculates the motion amount based on a difference between values of acoustic line signals corresponding to a same measurement point that are included in the frame acoustic line signals stored in the recording medium.

5. The ultrasound signal processing device of claim 3, wherein the sub-frame acoustic line signals, from which the frame acoustic line signal is generated, are generated based on the target area.

6. The ultrasound signal processing device of claim 1, wherein the motion amount calculator calculates the motion amount based on a plurality of the sub-frame acoustic line signals that have been generated in the past and are stored in a recording medium, and the target area setter provides the target area for one transmission event with reduced width in the transducer element array direction compared to the target area for a previous transmission event when the motion amount is equal to or greater than the predetermined threshold.

7. The ultrasound signal processing device of claim 6, wherein the motion amount calculator calculates the motion amount based on a difference between values of acoustic line signals corresponding to a same measurement point that are included in the sub-frame acoustic line signals stored in the recording medium.

8. The ultrasound signal processing device of claim 6, wherein when the target area setter provides the target area for the one transmission event with reduced width in the transducer element array direction compared to the target area for the previous transmission event, in the generation of the frame acoustic line signal, the synthesizer sets zero as a value of the sub-frame acoustic line signals for ones of the transmission events prior to the one transmission event.

9. The ultrasound signal processing device of claim 8, wherein
the sub-frame acoustic line signals, each of which corresponding to one of the transmission events, each include the acoustic line signals for measurement points that are included in the target area for the corresponding transmission event, and
the synthesizer generates the frame acoustic line signal by combining the sub-frame acoustic signals based on positions of measurement points from which the acoustic line signals included in the sub-frame acoustic line signals are acquired.

10. The ultrasound signal processing device of claim 2, wherein
the synthesizer generates the frame acoustic line signal by combining ones of the acoustic line signals corresponding to a same measurement point that are included in the sub-frame acoustic line signals.

11. The ultrasound signal processing device of claim 1, wherein
the target area setter provides the target area with minimum width in the transducer element array direction when the motion amount is equal to or greater than the predetermined threshold.

12. The ultrasound signal processing device of claim 1, wherein
the target area setter provides the target area for one transmission event with increased width in the transducer element array direction when the motion amount is smaller than the predetermined threshold, provided that the target area for a previous transmission event does not have maximum width in the transducer element array direction.

13. The ultrasound signal processing device of claim 1, wherein
the target area setter provides the target area with maximum width in the transducer element array direction when the motion amount is smaller than the predetermined threshold, provided that the target area set for a previous transmission event has the maximum width in the transducer element array direction.

14. The ultrasound signal processing device of claim 1, wherein
the target area setter sets the target area so as to be linear in shape, to be perpendicular to the transducer element array direction, and to pass through a center position of the first group of transducer elements in the transducer element array direction when the motion amount is equal to or greater than the predetermined threshold.

15. The ultrasound signal processing device of claim 1, wherein
the greater the motion amount, the smaller the number of acoustic line signals corresponding to a same measurement point that are included in the sub-frame acoustic line signals.

16. The ultrasound signal processing device of claim 2, wherein
the frame acoustic line signal is composed of a plurality of combined acoustic line signals, each of the combined acoustic line signals generated by combining ones of the acoustic line signals corresponding to a same measurement point that are included in the sub-frame acoustic line signals, and
the ultrasound signal processing circuitry further operates as
an amplifier that multiplies each of the combined acoustic line signals by an amplification factor determined based on a number of the ones of the acoustic line signals having been combined to yield the combined acoustic line signal.

17. The ultrasound signal processing device of claim 16, wherein
the target area has an hourglass shape, and a base of the target area is along a surface of the subject that comes in contact with the first group of transducer elements, and
different amplification factors are used for different depths in the subject.

18. The ultrasound signal processing device of claim 16, wherein
a difference between a lowest amplification factor and a highest amplification factor used for different depths in the subject is greater with a greater width of the target area in the transducer element array direction than with a reduced width of the target area.

19. The ultrasound signal processing device of claim 1, wherein
for each of the transmission events, the delay-and-sum processing is performed by using reception signal sequences acquired from an array of transducer elements whose center position corresponds to a center position of the first group of transducer elements for the transmission event.

20. The ultrasound signal processing device of claim 1, wherein
the delay-and-sum processing for each measurement point is performed by using reception signal sequences acquired from an array of transducer elements whose center position corresponds to one of the plurality of transducer elements that is spatially closest to the measurement point.

21. The ultrasound signal processing device of claim 1, wherein
the ultrasound signal processing circuitry further operates as
a weight calculator that calculates a weight sequence to be applied to an array of transducer elements from which the reception signal sequences with respect to which the delay-and-sum calculator performs the delay-and-sum processing are acquired, the weight sequence including the greatest weight for a transducer element located at a center position of the array of transducer elements, and
in the delay-and-sum processing for each measurement point, the delay-and-sum calculator, for each transducer element in the array of transducer elements, specifies a reception signal value corresponding to the measurement point and multiplies the specified reception signal value by a corresponding weight included in the weight sequence.

22. An ultrasound diagnostic device comprising
the ultrasound signal processing device of claim 1, and
the ultrasound probe, wherein
the ultrasound signal processing device is configured so that the ultrasound probe is connectable thereto.

23. The ultrasound signal processing device of claim 1, wherein the target area is hourglass-shaped or rectangular.

* * * * *